(12) United States Patent
Lee et al.

(10) Patent No.: US 6,468,766 B1
(45) Date of Patent: Oct. 22, 2002

(54) AORTIC CARBOXYPEPTIDASE-LIKE POLYPEPTIDE

(75) Inventors: Mu-En Lee, Newton; Matthew D. Layne, Brighton; Shaw-Fang Yet, Andover, all of MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/060,482

(22) Filed: Apr. 15, 1998

Related U.S. Application Data

(63) Continuation-in-part of application No. 08/818,009, filed on Mar. 14, 1997, now abandoned
(60) Provisional application No. 60/013,439, filed on Mar. 15, 1996.

(51) Int. Cl.$^7$ .......................... C12P 21/00; C12N 1/21; C12N 5/10; C07H 21/04; C07K 14/46
(52) U.S. Cl. ................... 435/69.1; 435/252.3; 435/325; 530/350; 536/23.5; 536/24.1
(58) Field of Search ............................ 435/69.1, 252.3, 435/320.1, 325; 530/350; 536/23.5, 24.3, 24.1

(56) References Cited

U.S. PATENT DOCUMENTS 5,460,951 A    10/1995   Kawai et al. .............. 435/69.1

FOREIGN PATENT DOCUMENTS

WO    WO 93/16178    *   8/1993

OTHER PUBLICATIONS

Sambrook et al. Molecular Cloning: A Laboratory Manual Second Edition vols. 1, 2 and 3. Cold Spring Harbor Laboratory Press: Cold Spring Harbor, New York, U.S.A. Nov., 1989, pp. 16.2 and 17.2.*

Alberts et al., Molecular Biology of the Cell, Jan. 1994, Garland Publishing, Inc., New York, NY, p. 119.*

Sambrook et al. Molecular Cloning: A Laboratory Manual Second Edition vols. 1, 2 and 3. Cold Spring Harbor Laboratory Press: Cold Spring Harbor, New York, U.S.A. Nov., 1989, pp. 9.50, 10.13 and 11.4.*

Meinkoth et al. Hybridization of nucleic acids immobilized on solid supports. Anal Biochem May 1984 1;138(2):267–284.*

New England Biolabs. 1995. Catalog #1014, p. 109.*

Natsuaki et al. Human skin mast cell carboxypeptidase: functional characterization, cDNA cloning, and genealogy. Journal of Investigative Dermatology, (Aug. 1992) 99 (2) 138–45.*

Blanar et al., "Interaction Cloning: Identification of a Helix–Loop–Helix Zipper Protein That Interacts with c–Fos", *Science* 256:1014–1018 (1992).

Blanar et al., "Meso1, a Basic–helix–Loop–Helix Protein Involved in Mammalian Presomitic Mesoderm Development", *PNAS USA* 92:5870–74 (1995).

Brendel et al., "Methods and Algorithms for Statistical Analysis of Protein Sequences", *PNAS USA* 89:2002–6 (1992).

Cool et al., "Carboxypeptidase E is a Regulated Secretory Pathway Sorting Receptor: Genetic Obliteration Leads to Endocrine Disorders in Cpe$^{fat}$ Mice", *Cell* 88:73–83 (1997).

Gerhard, "Fusion of Cells in Suspension and Outgrowth of Hybrids in Conditioned Medium", *Monoclonal Anti–bodies*: Hybridomas: A New Dimension in Biological Analyses, Plenum Press, pp. 370–371 (1980).

Gunther et al., "Functional Angiotnesin II Receptors in Cultured Vascular Smooth Muscle Cells", *J. Cell Biol.* 92:289–298 (1982).

He et al., "A Eukaryotic Transcriptional Repressor with Carboxypeptidase Activity", *Nature* 378:92–96 (1995).

He et al., "Neuropilin is a Receptor for the Axonal Chemorepellent Semaphorin III", *Cell* 90:739–751 (1997).

Hidai et al., "Cloning and Characterization of Development Endothelial Locus–1: An Embryonic Endothelial Cell Protein that Binds the αvβ3 Integrin Receptor", *Genes & Developmental* 12:21–33 (1998).

Hsieh et al., "APEG–1, a Novel Gene Preferentially Expressed in Aortic Smooth Muscle Cells, Is Down-regulated by Vascular Injury", *J. Biol. Chem.* 271(29):17354–59 (1996).

Jain et al., "In Vitro System for Differentiating Pluripotent Neural Crest Cells into Smooth Muscle Cells", *J. Biol. Chem.* 273(11):5993–96 (1998).

Johnson et al., "A Receptor Tyrosine Kinase Found in Breast Carcinoma Cells has an Extracellular Discoidin I–Like Domain", *PNAS USA* 90:5677–81 (1993).

Kane et al., "Cloning of a cDNA Coding for Human Factor V, a Blood Coagulation Factor Homologous to Factor VIII and Ceruloplasmin", *PNAS USA* 83:6800–4 (1986).

Kane et al., "Blood Coagulation Factors V and VIII: Structural and Functional Similarities and Their Relationship to Hemorrhagic and Thrombotic Disorders", *J. Amer. Soc. of Hematology* 71(3)539–55 (1988).

Kirby et al., "Role of Neural Crest in Congenital Heart Disease", *Circulation* 82:332–40 (1990).

(List continued on next page.)

Primary Examiner—David S. Romeo
(74) Attorney, Agent, or Firm—Ingrid A. Beattie; Mintz Levin Cohn Ferris Glovsky & Popeo

(57) ABSTRACT

The invention features a aortic carboxypeptidase-like polypeptide (ACLP), DNA encoding ACLP, and methods of detecting genetic alterations associated with abdominal wall defects.

11 Claims, 3 Drawing Sheets

OTHER PUBLICATIONS

Kirby et al., "Neural Crest and Cardiovascular Patterning", *Cir. Res.* 77(2):211–15 (1995).

Kohler et al., "Continuous Cultures of Fused Cells Secreting Antibody of Predefined Specificity", *Nature*, 256:495–497 (1975).

Kolodkin et al., "Neuropilin is a Semaphorin III Receptor", *Cell* 90:753–62 (1997).

Kozak, "Regulation of Translation in Eukaryotic Systems", *Ann. Rev. Cell Biol.* 8:197–225 (1992).

Larocca, et al., "A $M_r$ 46,000 Human Milk Fat Globule Protein That Is Highly Expressed in Human Breast Tumors Contains Factor VIII–like Domains", *Cancer Research* 51:4994–98 (1991).

Lee et al., "The Type I Iodothyronine 5'–Deiodinase Messenger Ribonucleic Acid Is Localized to the S3 Segment of the Rat Kidney Proximal Tubule", *Endocrinology* 132(5):2136–40 (1993).

Lee et al., "The High Affinity $Na^+$/Glucose Cotransporter", *J. Biol. Chem.* 269(16):12032–39 (1994).

Li et al., "Vascular Smooth Muscle Cells Grown on Matrigel", *J. Biol. Chem.* 269(30):19653–58 (1994).

Myers et al., "Detection of Single Base Substitutions by Ribonuclease Cleavage at Mismatches in RNA:DNA Duplexes," *Science* 230:1242–46 (1985).

Myers et al., "Detection and Localization of Single Base Changes by Denaturing Gradient Gel Electrophoresis", *Methods in Enzymology* 155:501–27 (1987).

Noden, "Embryonic Origins and Assembly of Blood Vessels", *Amer. Rev. of Respiratory Dis.* 140:1097–1103 (1989).

Ohno et al., "A cDNA Cloning of Human AEBP1 from Primary Cultured Osteoblasts and Its Expression in a Differentiating Osteoblastic Cell Line", *Biochem. Biophys. Res. Comm.* 288:411–14 (1996).

Orita et al., "Detection of Polymorphisms of Human DNA by Gel Electrophoresis as Single–strand Conformation Polymorphisms", *PNAS USA*, 86:2766–70 (1989).

Owens, "Regulation of Differentiation of Vascular Smooth Muscle Cells", *Physiological Reviews* 75:487–517 (1995).

Owens, "Expression of Smooth Muscle–specific α–Isoactin in Cultured Vascular Smooth Cells: Relationship Between Growth and Cytodifferentiation", *J. Cell Biol.* 102:343–52 (1986).

Pierschbacher et al., "The Cell Attachment Determinant In Fibronectin" *J. Cell. Biochem.* 28:115–126 (1985).

Roberts et al., "Localization of E2A mRNA Expression in Developing and Adult Rat Tissues", *PNAS USA* 90:7583–87 (1983).

Ross, "The Pathogenesis of Atherosclerosis: a Perspective for the 1990s", *Nature* 362:801–809 (1993).

Sheffield et al., "Attachment of a 40–base–pair G+C Rich Sequence (GC–clamp) to Genomic DNA Fragments by the the Polymerase Chain Reaction Results in Improved Detection . . . " *PNAS USA* 86:232–36 (1989).

Shrivastava et al., "An Orphan Receptor Tyrosine Kinase Family Whose Members Serve as Nonintegrin Collagen Receptors", *Molecular Cell*, 1:25–34 (1997).

Song et al., "Cloning and Expression of Human Carboxypeptidase Z, a Novel Metallocarboxy Peptidase", *J. Biol. Chem.* 272:10543–50 (1997).

Springer et al., "Discoidin I Is Implicated in Cell–Substratum Attachment and Ordered Cell Migration of Dictyostelium Discoideum and Resembles Fibronectin", *Cell* 39:557–64 (1984).

Stemple et al., "Isolation of a Stem Cell for Neurons and Glia from the Mammalian Neural Crest", *Cell* 71:973–85 (1992).

Stubbs et al., "cDNA Cloning of a Mouse Mammary Epithelial Cell Surface Protein Reveals the Existance of Epidermal Growth Factor–Like Domains Linked to Factor VIII–like Sequences", *PNAS USA* 87:8417–21 (1990).

Takagi et al., "The A5 Antigen, a Candidate for the Neuronal Recognition Molecule, Has Homologies to Complement Components and Coagulation Factors", *Neuron* 7:295–307 (1991).

Tan et al., "Induction of Heparin–Binding Epidermal Growth Factor–Like Growth Factor mRNA by Protein Kinase C Activators", *Kidney Int.* 46:690–95 (1994).

Toole et al., "Molecular Cloning of a cDNA Encoding Human Antihaemophilic Factor", *Nature* 312:342–47 (1984).

Topouzis et al., "Smooth Muscle Lineage Diversity in the Chick Embryo", *Dev. Biol.* 178:430–45 (1996).

Tracy et al., "Prothyrombinase Complex Assembly on the Platelet Surface is Mediated Through the 74,000–dalton Component of Factor $V_a$", *PNAS USA* 80:2380–84 (1983).

Vogel et al., "The Discooidin Domain Receptor Tyrosine Kinases Are Activated by Collagen", *Molecular Cell.* 1:13–23 (1997).

von Heijne, "Signal Sequences", *J. Mol. Biol.* 184:99–105 (1985).

White et al., "Detecting Single Base Substitutions as Heteroduplex Polymorphisms", *Genomics* 12:301–306 (1992).

Yoshizumi et al., "Tumor Necrosis Factor Increases Transcription of the Heparin–binding Epidermal Growth Factor–like Growth Factor Gene in Vascular Endothelial Cells", *J. Biol. Chem.* 267:9467–9469 (1992).

Yoshizumi et al., "Disappearance of Cyclin A Correlates with Permanent Withdrawal of Cardiomyocytes from the Cell Cycle in Human and Rat Hearts", *J. Clin. Invest.* 95:2275–80 (1995).

* cited by examiner

```
Human MAAVRGAPLLSCLLALLALCPGGRPQTVLTDDEIEEFLEGFLSELEPE..PREDDVEAPPPPEPTPRVRKAQAGGKPGKR   78
      ||:||.|.|::.|||||.|||:.||||||||||||||||||||:  |||||||..|  ||||.|.||..||||
Mouse MAPVRTASLLCGLLALLTLCPEGNPQTVLTDDEIEEFLEGFLSELETQSPPREDDVEVQPLPEPTQRPRKSKAGGK....    76

Human PGTAAEVPPEKTKDKGKKGKKDKGPKVPKESLEGSPRPPKKGKEKPPKATKKPKEKPPKATKKPKEEPPKATKKPKEKPP  158
      .....||||.|||:|||||||||..|  .||||.||.||.||||||||||||||||||||||.||||||||||||||||
Mouse QRADVEVPPEKNKDKEKKGKKDKGPKATK.PLEGSTRPTKKPKEKPPKATKKPKEKPPKATKKPKEKPPKATKKPKEKPP  155

Human KATKKPPSGKRPPILAPSETLEWPLPPPPSPGPEELPQEGGAPLSNNWQNPGEETHVEAQEHQPEPEEETEQPTLDYNDQ  238
      ||||:|..||:  ...:||  |||::  ||.|...|:::|||  :.|:.|:.||..||||:|||...||||||  ||||||
Mouse KATKRPSAGKKFSTVAPLETLDRLLPSPSNPSAQELPQKRDTPFPNAWQGQGEETQVEAKQPRPEPEEETEMPTLDYNDQ  235

Human IEREDYEDFEYIRRQKQPRPPPSRRRRPERVWPEPPEEKAPAPAPEERIEPPVKPLLPPLPPDYGDGYVIPNYDDMDYYF  318
      ||:|||||||||||||||.|||      |:|||.|||...|        :|||:|||    ||||||:||||||||:||||
Mouse IEKEDYEDFEYIRRQKQPRPTPSRR....RLWPERPEEKTEEPEERKEVEPPLKPL...LPPDYGDSYVIPNYDDLDYYF  308

Human GPPPPQKPDAERQTDEEKEELKKPKKEDSSPKEET.DKWAVEKGKDHKEPRKGEELEEEWTPTEKVKCPPIGMESHRIED  397
      ..||||||.::.||||||||||||||||..||||  |||.|||||||:|||||||||||||||||.||||||||||||||
Mouse PHPPPQKPDVGQEVDEEKEEMKKPKKEGSSPKEDTEDKWTVEKNKDHKGPRKGEELEEEWAPVEKIKCPPIGMESHRIED  388

Human NQIRASSMLRHGLGAQRGRLNMQTGATEDDYYDGAWCAEDDARTQWIEVDTRRTTRFTGVITQGRDSSIHDDFVTTFFVG  477
      ||||||||||||||||||||||||.||.|||||||||||:..||||||||||||||||||||||||||||||||||||||
Mouse NQIRASSMLRHGLGAQRGRLNMQAGANEDDYYDGAWCAEDESQTQWIEVDTRRTTRFTGVITQGRDSSIHDDFVTTFFVG  468

Human FSNDSQTWVMYTNGYEEMTFHGNVDKDTPVLSELPEPVVARFIRIYPLTWNGSLCMRLEVLGCSVAPVYSYYAQNEVVAT  557
      ||||||||||||||||||||.|||||||||||||||||||||||||||||||||||||||||.|.||||||||||||.|
Mouse FSNDSQTWVMYTNGYEEMTFYGNVDKDTPVLSELPEPVVARFIRIYPLTWNGSLCMRLEVLGCPVTPVSYYAQNEVVTT  548

Human DDLDFRHHSYKDMRQLMKVVNEECPTITRTYSLGKSSRGLKIYAMEISDNPGEHELGEPEFRYTAGIHGNEVLGRELLLL  637
      |.|||||||||||||||||.|||||||||||||||||||||||||||||||:||||||||||||||||||||||||||||
Mouse DSLDFRHHSYKDMRQLMKAVNEECPTITRTYSLGKSSRGLKIYAMEISDNPGDHELGEPEFRYTAGIHGNEVLGRELLLL  628

Human LMQYLCREYRDGNPRVRSLVQDTRIHLVPSLNPDGYEVAAQMGSEFGNWALGLWTEEGFDIFEDFPDLNSVLWGAEERKW  717
      ||||||.|||||||||||.||||||||||||||||||||||||||||||||||||||||||||||||||||||:|||:|
Mouse LMQYLCQEYRDGNPRVRNLVQDTRIHLVPSLNPDGYEVAAQMGSEFGNWALGLWTEEGFDIFEDFPDLNSVLWAAEEKKW  708

Human VPYRVPNNNLPIPERYLSPDATVSTEVRAIIAWMEKNPFVLGANLNGGERLVSYPYDMARTPTQEQLLAAAMAAARGEDE  797
      ||||||||||||||||||||||||||||||.||||||||||||||||||||||||||||||.|||||..|||||||:
Mouse VPYRVPNNNLPIPERYLSPDATVSTEVRAIISWMEKNPFVLGANLNGGERLVSYPYDMARTPSQEQLLAEALAAARGEDD  788

Human DEVSEAQETPDHAIFRWLAISFASAHLTLTEPYRGGCQAQDYTGGMGIVNGAKWNPRTGTINDFSYLHTNCLELSFYLGC  877
      |:|||||||||||||||||||||||||||:||||||||||||:|||||||||||||:|||:|||||||||||||.|||
Mouse DGVSEAQETPDHAIFRWLAISFASAHLTMTEPYRGGCQAQDYTSGMGIVNGAKWNPRSGTFNDFSYLHTNCLELSVYLGC  868

Human DKFPHESELPREWENNKEALLTFMEQVHRGIKGVVTDEQGIPIANATISVSGINHGVKTASGGDYWRILNPGEYRVTAHA  957
      ||||||||||||||||||||||||||||||||||||||||||||||||||||||||||||||||||||||||||||||||
Mouse DKFPHESELPREWENNKEALLTFMEQVHRGIKGVVTDEQGIPIANATISVSGINHGVKTASGGDYWRILNPGEYRVTAHA  948

Human EGYTPSAKTCNVDYDIGATQCNFILARSNWKRIREIMAMNGNRPIPHIDPSRPMTPQQRRLQQRRLQHRLRLRAQMRLRR 1037
      ||||.||||.||||||||||||||||||||||||||:||||||| :||||||||||||||||||||||.|||:|.|||||
Mouse EGYTSSAKICNVDYDIGATQCNFILARSNWKRIREILAMNGNRPILGVDPSRPMTPQQRRMQQRRLQYRLRMREQMRLRR 1028

Human LNATTTLGPHTVP.PTLPPAPATTLSTTIEPWGLIPPTTAGWEESETETYTEVVTEFGTEVEPEFGTKVEPEFETQLEPE 1116
      ||.|.  ||||  |.|.|:..|  .:  :::|.|||||||||||||||||||:|                         |
Mouse LNSTA..GPATSPTPALMPPPSPTPAITLRPWEVLPTTTAGWEESETETYTEVVTEFET.....................E 1086

Human FETQLEPEFEEEEEEKEEEIATGQAFPFTTVETYTVNFGDF  (SEQ ID NO:2)                         1158
      ::|:||.|  ||||||.|||:.  .|.|:||||||||||||
Mouse YGTDLEVEEIEEEEEEEEEMDTGLTFPLTTVETYTVNFGDF  (SEQ ID NO:8)                         1128
```

Fig. 1A

AORTIC CARBOXYPEPTIDASE-LIKE POLYPEPTIDE

CROSS REFERENCE TO RELATED APPLICATIONS

This application is a continuation-in-part of, and claims priority from application U.S. Ser. No. 08/818,009 filed on Mar. 14, 1997 now abandoned, which claims priority from provisional application U.S. Ser. No. 60/013,439, filed on Mar. 15, 1996, both of which are hereby incorporated by reference.

STATEMENT AS TO FEDERALLY SPONSORED RESEARCH

This invention was funded in part by the U.S. Government under grant numbers RO1GM awarded by the National Institutes of Health. The Government has certain rights in the invention.

BACKGROUND OF THE INVENTION

The invention relates to gastrointestinal abnormalities.

Gastroschisis is a life-threatening abdominal wall defect that occurs in approximately 1–7 of every 10,000 human births. The defect is thought to originate on the right side of the umbilical cord and may involve the formation of the omphalomesenteric artery. Infants with gastroschisis can be born with abdominal organs outside the body cavity, i.e., protruding through the defect. Factors associated with an increased risk for gastroschisis include a maternal age below 20 years, ingestion of aspirin, and ingestion of pseudoephedrine. The cause of gastroschisis has not been identified.

SUMMARY OF THE INVENTION

A novel human gene encoding aortic carboxypeptidase-like polypeptide (ACLP) has been discovered. A mutation in an ACLP gene has now been shown to be associated with the development of gastroschisis. Thus, a mutation in an ACLP gene is indicative of gastroschisis or a predisposition to develop the condition. Accordingly, the invention provides an isolated nucleic acid (e.g., genomic DNA, cDNA, or synthetic DNA) encoding an ACLP. By the term "human ACLP" is meant a polypeptide having the amino acid sequence of a naturally-occurring human ACLP. For example, the invention encompasses an ACLP with the amino acid sequence of SEQ ID NO:2 as well as naturally-occurring variants thereof such as mutant forms associated with gastroschisis or isoforms resulting from alternative splicing of exons of the ACLP gene.

The invention includes a nucleic acid molecule which contains the nucleotide sequence of human ACLP cDNA (SEQ ID NO:1). A nucleic acid molecule which contains nucleotides 140–3613 (ACLP coding sequence), inclusive, of SEQ ID NO:1 or a degenerate variant thereof, is also within the invention. Nucleotides 214–3613 encode an ACLP which lacks the first 25 residues (a putative signal peptide). Preferably, the nucleic acid molecule contains a nucleotide sequence encoding a polypeptide having an amino acid sequence that is at least 87% identical to the sequence of SEQ ID NO:2. More preferably, the sequence is at least 90% identical to SEQ ID NO:2, more preferably at least 95%, more preferably at least 98%, more preferably at least 99%, and most preferably, the nucleotide sequence encodes a polypeptide the amino acid sequence of which is SEQ ID NO:2.

An isolated nucleic acid molecule containing a strand which hybridizes at high stringency to a DNA having the sequence of SEQ ID NO:1, or the complement thereof is also within the invention. The nucleic acid molecule may be a primer useful to amplify ACLP DNA in a polymerase chain reaction (PCR). For example, the nucleic acid is at least 5 nucleotides but less than 50 nucleotides in length. Alternatively, the nucleic acid molecule may encompass the entire coding sequence of ACLP CDNA, i.e., nucleotides 140–3613, inclusive, of SEQ ID NO:1. Preferably, the nucleic acid molecule spans a gastroschisis-associated mutation in an ACLP gene. Such a molecule is useful as a hybridization probe to identify a genetic alteration, e.g., a deletion, duplication, point mutation, or translocation, that indicates that an individual has gastroschisis, is predisposed to developing gastroschisis, or is a heterozygous carrier of a genetic alteration associated with gastroschisis.

By "isolated nucleic acid molecule" is meant a nucleic acid molecule that is free of the genes which, in the naturally-occurring genome of the organism, flank an ACLP gene. The term therefore includes, for example, a recombinant DNA which is incorporated into a vector; into an autonomously replicating plasmid or virus; or into the genomic DNA of a procaryote or eucaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence. The term excludes large segments of genomic DNA, e.g., such as those present in cosmid clones, which contain an ACLP gene flanked by one or more other genes which naturally flank it in a naturally-occurring genome.

Nucleic acid molecules include both RNA and DNA, including cDNA, genomic DNA, and synthetic (e.g., chemically synthesized) DNA. Where single-stranded, the nucleic acid molecule may be a sense strand or an antisense strand. The term therefore includes, for example, a recombinant DNA which is incorporated into a vector, into an autonomously replicating plasmid or virus, or into the genomic DNA of a procaryote or eucaryote at a site other than its natural site; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence.

Hybridization is carried out using standard techniques such as those described in Ausubel et al., *Current Protocols in Molecular Biology*, John Wiley & Sons, (1989). "High stringency" refers to DNA hybridization and wash conditions characterized by high temperature and low salt concentration, e.g., hybridization and wash conditions of 65° C. at a salt concentration of 0.1×SSC. "Low" to "moderate" stringency refers to DNA hybridization and wash conditions characterized by low temperature and high salt concentration, e.g. wash conditions of less than 60° C. at a salt concentration of at least 1.0×SSC. For example, high stringency conditions may include hybridization at 42° C. in a solution containing 50% formamide; a first wash at 65° C. using a solution of 2×SSC and 1% SDS; followed by a second wash at 65° C. using a solution of 0.1%×SSC. Lower stringency conditions suitable for detecting DNA sequences having about 50% sequence identity to an ACLP gene are detected by, for example, hybridization at 42° C. in the absence of formamide; a first wash at 2° C. in a solution of 6×SSC and 1% SDS; and a second wash at 50° C. in a solution of 6×SSC and 1% SDS.

TABLE 1

Human ACLP cDNA

```
   1 tccctcgctc accccatcct ctctcccgcc ccttcctgga ttccctcacc cgtctcgatc
  61 ccctctccgc cctttcccag agacccagag ccctgaccc cccgcgccct ccccggagcc
 121 ccccgcgcgt gccgcggcca tggcggccgt gcgcggggcg ccctgctca gctgcctcct
 181 ggcgttgctg gccctgtgcc ctggagggcg cccgcagacg gtgctgaccg acgacgagat
 241 cgaggagttc ctcgagggct tcctgtcaya gctagaacct gagccccggg aggacgacgt
 301 ggaggccccg ccgcctcccg agcccacccc gcgggtccga aaagcccagg cggygggcaa
 361 gccagggaag cggccaggga cggccycaga agtgcctccg gaaaagacca aagacaaagg
 421 gaagaaaggc aagaaagaca aaggcccaa ggtgcccaag gagtccttgg aggggtcccc
 481 caggccgccc aagaagggga aggagaagcc acccaaggcc accaagaagc ccaaggagaa
 541 gccacctaag yccaccaaga ayccaagga ggagccaccc aaggccacca agaagcccaa
 601 agagaagcca cccaaggcca ccaagaagcc ccgtcaggg aagaggcccc ccattctggc
 661 tccctcagaa accctggagt ggccactgcc cccacccccc agccctggcc ccgaggagct
 721 accccaggag ggaggggcgc ccctctcaaa taactggcay aatccaggag aggagaccca
 781 tgtggaggca caggagcacc agcctgagcc ggaggaggag accgagcaac ccacactgga
 841 ctacaatgac cagatcgaga gggaggacta tgaggacttt gagtacattc ggcgccagaa
 901 gcaacccagg ccaccccaa gcagaaggag gaggcccgag cgggtctggc cagagccccc
 961 tgaggagaag gccccggccc cagcccccgga ggagaggatt gagcctcctg tyaagcctct
1021 gctgccccg ctgcccctg actatggtga tggttacgtg atccccaact acgatgacat
1081 ggactattac tttgggcctc ctccgcccca gaagcccgat gctgagcgcc agacggacga
1141 agagaaggag gagctgaaga aacccaaaaa ggaggacagc agcccaagg aygagaccga
1201 caagtgggca gtggagaagg gcaaggacca caaagagccc cgaaaggycg aggagttgga
1261 ggaggagtgg acgcctacgg agaaagtcaa gtgtcccccc attgggatgg aytcacaccg
1321 tattgaggac aaccagatcc gagcctcctc catgctgcgc cacygcctgg gggcacagcg
1381 cggccggctc aacatgcaga ccgtgccac tgaggacgac tactatgatg gtgcgtggtg
1441 tgccgaggac gatgccagga cccagtggat agaggtggac accaggagga ctacccggtt
1501 cacaggcgtc atcacccagg gcagagactc cagcatccat gacgattttg tgaccaccctt
1561 cttcgtgggc ttcagcaatg acagccagac atgggtgatg tacaccaacg gctatgagga
1621 aatgaccttt catgggaacg tggacaagga cacaccgtg ctgagtgagc tcccagagcc
1681 ggtggtggct cgtttcatcc gcatctaccc actcacctgg aatggcagcc tgtgcatgcg
1741 cctgaggtg ctggggtgct ctgtggcccc tytctacagc tactacgcac agaatgaggt
1801 ggtggccacc gatgacctgg atttccggca ccacagctac aaggacatgc gccagctcat
1861 gaaggtggtg aacgaggagt gccccaccat caccgcact tacagcctgg gcaagagctc
1921 acgaggcctc aagatctatg ccatggagat ctcagacaac cctggggagc atgaactggg
1981 ggagcccgag ttccgctaca ctgctgggat ccatggcaac gaggtgctgg gccgagagct
2041 gttgctgctg ctcatgcagt acctgtgccg agagtaccgc gatgggaacc cacgtgtgcg
2101 cagcctggtg caggacacac gcatccacct ggtgccctca ctgaaccctg atggctacga
2161 ggtggcagcg cagatgggct cagagtttgg gaactgggcg ctgggactgt ggactgagga
2221 gggctttgac atctttgaag atttcccgga tctcaactct gtyctctggg gagctgagga
2281 gaggaaatgg gtcccctacc gggtcccaa caataacttg cccatccctg aacgctacct
2341 ttcgccagat gccacggtat ccacggaggt ccgggccatc attgcctgga tggagaagaa
2401 cccttcgtg ctgggagcaa atctgaacgg cggcgagcgg ctagtatcct acccctacga
2461 tatgcccgc acgcctaccc aggagcagct gctggccgca gccatggcag cagcccgggg
2521 ggaggatgag gacgaggtct ccgaggccca ggagactcca gaccacgcca tcttccggtg
2581 gcttgccatc tccttcgcct ccgcacacct caccttgacc gagccctacc gcggaygctg
2641 ccaagcccag gactacaccg gcggcatggg catcgtcaac ggggcaagt ggaaccccg
2701 gaccgggact atcaatgact tcagttacct gcataccaac tgcctggagc tctccttcta
2761 cctgggctgt gacaagttcc tcatgagag tgagctgccc cgcgagtggg agaacaacaa
2821 ggaggcgctg ctcaccttca tggagcaggt gcaccgcggc attaayyggg tggtgacgga
2881 cgagcaaggc atcccccattg ccaacgccac catctctgtg agtggcatta atcacggcgt
2941 gaagacagcc agtggtggtg attactggcg aatcttgaac ccgggtgagt accgcgtgac
3001 agcccacgcg gagggctaca ccccgagcgc caagacctgc aatgttgact atgacatcgg
3061 ggccactcag tgcaacttca tcctggctcg ctccaactgg aagcgcatcc gggagatcat
3121 ggccatgaac gggaaccggc ctatcccaca catagcccca tcgcgcccta tgacccccca
3181 acagcgacgc ctgcagcagc gacgcctaca acaccgcctg cggcttcggg cacagatgcg
3241 gctgccggcgc ctcaacgcca ccaccaccct aggccccccac actgtgcctc ccacgctgcc
3301 ccctgcccct gccaccaccc tgagcactac catagagccc tggggcctca taccgccaac
3361 caccgctggc tgggaggagt cggagactga gacctacaca gaggtggtga cagagtttgg
3421 gaccgaggtg gagcccgagt ttgggaccaa ggtggagccc gagtttgaga cccagttgga
3481 gcctgagttc gagacccagc tggaacccga gtttgaggaa gaggaggagg aggagaaaga
3541 ggaggagata gccactggcc aggcattccc cttcacaaca gtagagacct acacagtgaa
3601 ctttggggac ttctgagatc agcgtcctac caagacccca gcccaactca agctacagca
3661 gcagcacttc ccaagcctgc tgaccacagt cacatcaccc atcagcacat ggaaggcccc
3721 tggtatggac actgaaagga agggctggtc ctgcccctt gagggggtgc aaacatgact
3781 gggacctaag agccagaggc tgtgtagagg ctcctgctcc acctgccagt ctcgtaagag
3841 atggggttgc tgcagtgttg gagtaggggc agagggaggg agccaaggtc actccaataa
3901 aacaagctca tggcaaaaaa aaaaaaaaaa aaaaa (SEQ ID NO:1)
```

The invention also includes a substantially pure human ACLP polypeptide. A substantially pure ACLP polypeptide may be obtained, for example, by extraction from a natural source (e.g., a vascular smooth muscle cell); by expression of a recombinant nucleic acid encoding an ACLP; or by chemically synthesizing the protein. A polypeptide or protein is substantially pure when it is separated from those contaminants which accompany it in its natural state (proteins and other naturally-occurring organic molecules). Typically, the polypeptide is substantially pure when it constitutes at least 60%, by weight, of the protein in the preparation. Preferably, the protein in the preparation is at least 75%, more preferably at least 90%, and most preferably at least 99%, by weight, ACLP. A substantially pure ACLP may be obtained, for example, by extraction from a natural source (e.g., a vascular smooth muscle cell); by expression of a recombinant nucleic acid encoding an ACLP; or by chemically synthesizing the protein. Purity can be measured by any appropriate method, e.g., column chromatography, polyacrylamide gel electrophoresis, or HPLC analysis. Accordingly, substantially pure polypeptides include recombinant polypeptides derived from a eucaryote but produced in E. coli or another procaryote, or in a eucaryote other than that from which the polypeptide was originally derived.

For expression of recombinant ACLP, an ACLP-encoding nucleic acidc is operably linked to a regulatory sequence, e.g., a promoter. By "promoter" is meant a minimal DNA sequence sufficient to direct transcription. Promoters may be constitutive or inducible, and may be coupled to other regulatory sequences or "elements" which render promoter-dependent gene expression cell-type specific, tissue-specific or inducible by external signals or agents; such elements may be located in the 5' or 3' region of the native gene, or within an intron. DNA encoding an ACLP may be operably linked to such regulatory sequences for expression of the polypeptide in procaryotic or eucaryotic cells. By "operably linked" is meant that a coding sequence and a regulatory sequence(s) are connected in such a way as to permit gene expression when the appropriate molecules (e.g., transcriptional activator proteins) are bound to the regulatory sequence(s).

To produce recombinant ACLP, a cell containing an ACLP-encoding sequence operably linked to appropriate regulatory sequences is cultured under conditions permitting expression of a nucleic acid molecule. The cell may be a procaryotic cell or a eucaryotic cell. To obtain post-translationally modified, e.g., glycosylated recombinant ACLP, the recombinant polypeptide is produced in a eucaryotic cell, e.g., a yeast or mammalian cell.

An ACLP preferably contains an amino acid sequence that is at least 87% identical to the amino acid sequence of SEQ ID NO:2. More preferably, the amino acid sequence is at least 90% (more preferably at least 95%, more preferably at least 98%, more preferably at least 99%) identical to SEQ ID NO:2. Most preferably, the polypeptide contains the amino acid sequence of SEQ ID NO:2.

The invention also includes polypeptides which contain a portion of naturally-occurring ACLP, e.g., an ACLP fragment containing a lysine-rich/proline rich domain (amino acids 117–164 of SEQ ID NO:2), an ACLP fragment containing a discoidin-like domain (amino acids 385–540 of SEQ ID NO:2), or an ACLP fragment containing a carboxypeptidase-like domain (amino acids 562–969 of SEQ ID NO:2).

Where a particular polypeptide or nucleic acid molecule is said to have a specific percent identity to a reference polypeptide or nucleic acid molecule of a defined length, the percent identity is relative to the reference polypeptide or nucleic acid molecule. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, many other polypeptides will meet the same criteria. The same rule applies for nucleic acid molecules.

For polypeptides, the length of the reference polypeptide sequence will generally be at least 10 amino acids, preferably at least 20 amino acids, more preferably at least 25 amino acids, and most preferably 35 amino acids, 50 amino acids, or 100 amino acids. For nucleic acids, the length of the reference nucleic acid sequence will generally be at least 25 nucleotides, preferably at least 50 nucleotides, more preferably at least 75 nucleotides, and most preferably 100 nucleotides or 300 nucleotides.

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Sequence identity can be measured using sequence analysis software (for example, the Sequence Analysis Software Package of the Genetics Computer Group, University of Wisconsin Biotechnology Center, 1710 University Avenue, Madison, Wis. 53705), with the default parameters as specified therein.

TABLE 2

Human ACLP amino acid sequence

MAAVRGAPLLSCLLALLALCPGGRPQTVLTDDEIEEFLEGFLSELEPEPREDDVEAPPPP
EPTPRVRKAQAGGKPGKRPGTAAEVPPEKTKDKGKKGKKDKGPKVPKESLEGSPRPPKKG
KEKPPKATKKPKEKPPKATKKPKEEPPKATKKPKEKPPKATKKPPSGKRPPILAPSETLE
WPLPPPPSPGPEELPQEGGAPLSNNWQNPGEETHVEAQEHQPEPEEETEQPTLDYNDQIE
REDYEDFEYIRRQKQPRPPPSRRRRPERVWPEPPEEKAPAPAPEERIEPPVKPLLPPLPP
DYGDGYVIPNYDDMDYYFGPPPPQKPDAERQTDEEKEELKKPKKEDSSPKEETDKWAVEK
GKDHKEPRKGEELEEEWTPTEKVKCPPIGMESHRIEDNQIRASSMLRHGLGAQRGRLNMQ
TGATEDDYYDGAWCAEDDARTQWIEVDTRRTTRFTGVITQGRDSSIHDDFVTTFFVGFSN
DSQTWVMYTNGYEEMTFHGNVDKDTPVLSELPEPVVARFIRIYPLTWNGSLCMRLEVLGC
SVAPVYSYYAQNEVVATDDLDFRHHSYKDMRQLMKVVNEECPTITRTYSLGKSSRGLKIY
AMEISDNPGEHELGEPEFRYTAGIHGNEVLGRELLLLLMQYLCREYRDGNPRVRSLVQDT
RIHLVPSLNPDGYEVAAQMGSEFGNWALGLWTEEGFDIFEDFPDLNSVLWGAEERKWVPY
RVPNNNLPIPERYLSPDATVSTEVRAIIAWMEKNPFVLGANLNGGERLVSYPYDMARTPT
QEQLLAAAMAAARGEDEDEVSEAQETPDHAIFRWLAISFASAHLTLTEPYRGGCQAQDYT
GGMGIVNGAKWNPRTGTINDFSYLHTNCLELSFYLGCDKFPHESELPREWENNKEALLTF
MEQVHRGIKGVVTDEQGIPIANATISVSGINHGVKTASGGDYWRILNPGEYRVTAHAEGY
TPSAKTCNVDYDIGATQCNFILARSNWKRIREIMAMNGNRPIPHIDPSRPMTPQQRRLQQ
RRLQHRLRLRAQMRLRRLNATTTLGPHTVPPTLPPAPATTLSTTIEPWGLIPPTTAGWEE
SETETYTEVVTEFGTEVEPEFGTKVEPEFETQLEPEFETQLEPEFEEEEEEKEEEIATG
QAFPFTTVETYTVNFGDF (SEQ ID NO:2)

A substantially pure DNA containing an ACLP promoter/enhancer sequence (SEQ ID NO:3) is useful for directing transcription of DNA encoding all or part of ACLP or of DNA encoding a heterologous polypeptide (e.g., a polypeptide other than ACLP or an ACLP the sequence of which corresponds to a naturally-occurring ACLP of a species other than the species from which the promoter/enhancer sequence is derived). For example, a murine ACLP promoter/enhancer sequence may be operably linked to DNA encoding human ACLP for therapeutic expression of ACLP in human patients. To regulate transcription of the polypeptide-encoding sequence (e.g., developmental stage-specific transcription), the promoter/enhancer sequence is operably linked to a polypeptide-encoding sequence. The ACLP promoter/enhancer sequence directs transcription of a polypeptide-encoding sequence.

By "promoter/enhancer sequence" is meant a DNA sequence located 5' to the transcriptional start site of the ACLP gene and which contains one or more cis-acting elements which regulate transcription, e.g., cell specific transcription. The elements may be contiguous or separated by DNA not involved in the regulation of transcription, e.g., an enhancer element may be in a position immediately adjacent to the promoter element or up to several kilobases upstream or downstream of the transcriptional start site. The promoter/enhancer DNA is preferably derived from the 5' region of a mammalian ACLP gene, such as that of the mouse (SEQ ID NO:3), and regulates expression of a polypeptide-encoding DNA to which it is operably linked. The promoter/enhancer sequence regulates developmental stage-specific expression, e.g., expression in embryonic cells, of a polypeptide-encoding sequence.

TABLE 3

Mouse ACLP promoter/enhancer

AAGCTTAGTCTCCCTCTCTCCTGGCTCCTCTCCTGGGGCTTCCCTATGGAGGTAGCACTT
ACAGAAGATGCTTGTTCCAAACCTTCAGGGGTACAAACTACACAGATATACTGAAGGACA
GGAGGCTGGGGCCTCCCCCCACCCCCAACAGCCACTGTTCTCTCAGGAGCTCTGCTTCTG
CTCTGCAGCATTGAAAACAAAACTGAAGGACACCTTCCTTCTCTCAGGCCAGCCCAGTGC
TGTTGTGTGATCCCTCGGGAAGACTCTAACGCATTCACAGGGACAACAGGAGTTGGGAGG
GAGAGGAGTTACAGAACTTTCCAGCAGGACCTCAGGAGAACGCCTGGACACGGACAGGAA
CCCCCAACCCCTCAGGGACCCCCTTGGACCCTTTGAGTGCTCCTGATCATGGAAGCCACC
AGCCTCCCGATTCCTCAGCTGTGGCCTTGGCAGTGCCCTCTGGACATTTGACTTAAACGC
TATGCTCTTCAGCAGAGTGGAGAGCTCTCCTCACAGGCTCTGGCTTCTGGTTGTCCTCTT
GCCCCAGCGCTGTGGGCCCAGGTTAGAAAGACTTCCTGAGGACAGGCTCCCTCAGGAGGA
TCCCCAGCGTACGACTGTGCTCCCACGCACCTTTCCGGATTTTCTGTGTGGAGGCCTCAA
CCCCTCAGGCCTCCTGGGCCAGCTCCTCTGCTCGAATTCCTGTCCGTGACTCATTGAGGC
TCAGGAAAAGGCTTTCTAGACCTTAGGTTTCTTTGTTTTCCATTTTTGAAATGGCTTCTG
TTTTCCCTGGCAGAGAATATCCAACCCAAATTCAGTCCAAGTATGACCCATGCCTAGGGA
AGTGACATCCATGTCCCCTCATGCACCCTGTGGCATACCCAGCATGACACACTGGACCAG
ACTGGGGGCACGGAAGCCAATTCCCAGAACTGACTTTGAGCACAATGATTCAGAGGGTGA
CCATGAGTGAGACTTGCTTTACTCTTGCTCTGCGACCAGGTTGAAGTCTCTCATGGGGAG
GCCTAGCTGTGAGAGGATTGTCCTGGGATGGGGGAAGGGGGAGCAAAGTGGATGAGGACC
AACAGCCTGTGGGATGCAAGGGCTGATCGTGTGTGCTAGGCACAGCACAAAGTGGTCCAT
TTAGCCGGGCAGTGGTGGTGCACACCTTTAATCCCAGCACTTGGGAGGCAGCAGCAGGTG
GGTTTCTGAGTTCGAGGCCAGCCTGGTCTACAGAGCAAGTTCCAGGACAGCCAGAGCTAC
ACAGAGAAACTCTGTCTCAAAAAAATCGAATAAACCAGAAAGGTGGTCCATTTAATATGC
GTATAGTAAGTTGTGGACACGGGAGTTCCCCTGCTGAGTCAGACAGCTAGGAGGGCTAAG
ATGGGTTAGACCCTCCCCCCCCCCACACACACACACACACACTCACACACACATCAGTTC
TTGGCATAGTCTCCATGCTTCCTCAAGGAGAGCCAGAAAGGAGACTGCCGGGAGGAGCTT
GCCTACTCCCTGAGAGCAGTGGGTTACAGAGCCCAGTGCCCGAAAATTTCCCCTTTTTCT
CCCTGCTCATGCTGGACAGAGAGGGTGAGGGTGAGGGTGAAAGACTGAGGAGGTGGCATC
GTGTTGGTGTTTCTTGACCTGCTTTTTCTTTTTTCTCTTCCAGCTGAGATGTAAACTTTC
CCATGTCAATCATCTGGGGGTCGCTATTCTTTTTTATCAGAGTGCCTCCCCACCTTGGTT
GAAAGCTGCCTGCCACTACCCTGGACCTATGGCTGCTACAAGCCCACGTTCACATCTTTA
ATCCTTCATGGGTAAATGCTCTGGCATTCCTGGGCTTAGCTATGATGGCCATTATGAGCC
AGCCAACGTTTGTATTCTAGAAGCCATAGCTGAAGCTGTTGTAAACAATTTGTTGTTTTA
ACCGCTTCTGGTCAGAGGAAGGAGAGAATAGCTATTACTCCACATTGGGACCTGAGCCCT
GAGCTCTGAAGTGGGGCTCCTATCTCCATAAGGACAGCAGCTTGCTGAGAACAGCTTTTC
ACAGCCTTCCTCGCAAAAATTGGCTCCAAAGACCTGGGATGTTGGTGATAACTGGACAAA
GGTGACACCTGTGCAAGCACACAGCAGGTGACACTTTGAAGAGCTAACCTCCAGAAAGTG
GAAAGGAGGTGATCGCCAGTACCCTCGAGGGCCCTACTCCCTCCCTCCCCTAGCAATCTC
CCTGGGCTCAGAGCAAAGGGCACAGCGGGTTAGAGCACAGGTCTCCTTAGACTCCGCACA
CTCCCTTCCCCATAACTGTTGCATTCTTTTCTCCCAGGCCTTCCTCCCCGCTAGGCGCCC
TGCACCCAGACCCTCTAAACTGGCGCGTGACGCTGCTATTAGTCTGGGCTCCGTGCTGTC
CGCCTCCCTCCCCCGCAGCCCCGGTCCAAGGCCGGCTCCTCCTCCTCCCCCTCCGGAAA
CCCGAAGCCCCCGCCCCGGCCAGGCCGTCGCAAGCGCTCTGGAGGGCGGTCCGCGTGAGA
GCCAGCCACGCGGGGCAGGAGCGCCCAGTTGCTGCCGGAGCTGGGCCCGCCAGAACCTCT
CCTGGAGCCCCTTGCTCTCCTTGAATCTCCCTTTCCCACCGCTTTCTGGATACCCTTGAC
GCCCACGTTCCTCGCGCCCTTTCCCGCCCCTACGCGGGGCGCTGCCCCTGCCACCCAAGT
CCCTGCTCAAGCCCGCCCGGTCCCGCGCGTGCCCAGAGCCATG (SEQ ID NO: 3)

The invention also includes a vector containing the promoter/enhancer DNA of the invention (operably linked to a polypeptide-encoding DNA sequence), and a vascular smooth muscle cell containing the vector. Also within the invention is a method of directing vascular smooth cell-specific expression of the polypeptide by introducing the vector into a vascular smooth muscle cell and maintaining the cell under conditions which permit expression of the polypeptide, e.g., introducing the vector into a human patient for gene therapy.

A method of detecting a gastroschisis-associated genetic alteration is carried out by providing a sample of DNA or RNA from a patient or fetus, and determining whether the DNA or RNA contains a mutation in a gene encoding an ACLP. Detection of such an ACLP mutation indicates that the patient or fetus has a genetic alteration that is associated with the development of gastroschisis. The presence of a gastroschisis-associated genetic alteration is diagnostic of gastroschisis or a predisposition to developing gastroschisis. The method can also be used to identify heterozygous carriers of a mutation associated with gastroschisis. Such individuals may be asymptomatic but are at risk of having children which are homozygous for an ACLP mutation (and therefore, likely to develop clinical gastroschisis). Tissue samples from adult patients are obtained by conventional means, e.g., biopsy or venipuncture. Prenatal testing is carried out by obtaining fetal tissue samples, e.g., by amniocentesis or chorionic villi sampling.

Patient-derived DNA is examined for genetic abnormalities in the ACLP gene, e.g., by detecting restriction fragment length polymorphisms (RFLPs), deletions, point mutations, or other defects. The diagnostic method includes the step of subjecting the sample to polymerase chain reaction (PCR), using a forward PCR primer complementary to a portion of the antisense strand of the gene, the portion being within (a) a first intron of the gene, or (b) the 5' untranslated region adjacent to the start codon of the gene; and a reverse PCR primer complementary to a fragment of the sense strand of the gene, this fragment being within (a) a second intron of the gene, or (b) the 3' untranslated region adjacent to the termination codon of the gene. PCR can also be used to detect mutations in an ACLP promoter or other regulatory sequences using primers that flank the mutation. ACLP mutations and/or aberrant ACLP expression can also be detected using standard hybridization techniques, such as Northern blotting.

Fragments of ACLP are useful to raise ACLP-specific antibodies. Accordingly, the invention includes an antibody, e.g., a polyclonal antisera or a monoclonal antibody preparation, that selectively binds to an ACLP. ACLP-specific antibodies are used to diagnose gastroschisis or a predisposition thereto. For example, a diagnostic method is carried out by providing a tissue sample from a patient or fetus, and detecting expression of an ACLP gene in the tissue sample. Expression is measured by detecting the amount of ACLP-specific antibody that binds to the tissue sample, e.g., by ELISA assay, Western blot assay, or immunohistochemical staining of tissue sections. Expression of ACLP is also measured by detecting the level of ACLP transcript in the tissue sample. Regardless of the method of detection of ACLP expression, a reduction in the amount of expression in the patient-derived tissue sample compared to the level of expression in a normal control tissue sample indicates that the patient or fetus from which the sample was obtained has or is predisposed to developing gastroschisis.

Methods of treating or preventing the development of gastroschisis are also within the invention. For example, one treatment regimen includes the steps of identifying a patient with or at risk of developing gastroschisis, and introducing into cells of the patient an isolated nucleic acid encoding ACLP, e.g., a nucleic acid which contains the nucleotide sequence of 140 to 3613 of SEQ ID NO:1. The cells into which the DNA was introduced produce the recombinant ACLP to compensate for a gastroschisis-associated genetic alteration, e.g., a mutation resulting in reduced production of ACLP or a mutation resulting in the production of a defective ACLP. Rather than administering ACLP-encoding DNA to the patient, an ACLP (e.g., a polypeptide having the sequence of SEQ ID NO:2) or a fragment thereof may be introduced into the patient.

An animal model for gastroschisis is useful to study the development of the condition as well as to evaluate therapeutic approaches to treatment or prevention of gastroschisis. A genetically-altered non-human mammal, all diploid cells of which contain a mutation in an endogenous gene encoding an ACLP, is included in the invention. For example, a mammal with a homozygous null mutation in its ACLP gene(s) develops gastroschisis. Preferably, the mammal is a rodent such as a mouse. The genetically altered non-human mammal produces altered levels of ACLP or mutant forms of ACLP. The levels of ACLP gene product in the genetically altered mammal can be increased or decreased at different time periods during development. By "genetically altered mammal" is meant a mammal in which the genomic DNA sequence has been manipulated in some way. The genetically altered mammal may be a knockout in which the endogenous ACLP sequences have been deleted or otherwise altered to decrease or change the pattern of expression. Alternatively, the genetically altered mammal may be transgenic. For example, the transgenic mammal may express ACLP sequences from another species, may overexpress ACLP gene product, or may express ACLP in tissues and at developmental stages other than those in which ACLP is expressed in a wild type animal.

The nucleated cells of a genetically altered mammal not producing a functional endogenous ACLP may be engineered to encode a human ACLP, and to express functional human ACLP, or, alternatively, ACLP from another heterologous species.

Preferably, the genetically altered non-human mammal is a rodent such as a mouse or a rat, the germ cells and somatic cells of which contain a mutation in DNA encoding ACLP. All diploid cells of such an animal contain a mutation in one or both alleles of the endogenous ACLP gene. The mutation can, for example, be a deletion, an insertion, or a nucleotide substitution. The mutation could be in the ACLP regulatory regions or in the coding sequence. It can, e.g., introduce a stop codon that results in production of a truncated, inactive gene product or it can be a deletion of all or a substantial portion of the coding sequence. For example, one or more exons, e.g., exons 7–15, of an ACLP gene may be deleted. By the term "null mutation" is meant a mutation that reduces the expression or activity level of the protein encoded by the mutated gene by more than 80% relative to the unmutated gene. A mouse harboring such a null mutation is a knockout mouse. An ACLP knockout mouse, i.e., one that harbors a homozygous ACLP null mutation, has been found to have an abdominal defect with an extrusion of abdominal organs i.e., gastroschisis.

The invention also includes a mammalian cell line, e.g., immortalized ACLP deficient cells, the genomic DNA of which contains a null mutation in DNA encoding ACLP. Such cells lack the ability to synthesize full length functional ACLP. The cells harboring the null mutation may be derived from a cell obtained from a ACLP deficient mammal, e.g., an ACLP knockout mouse.

Compounds capable of promoting expression or function of an ACLP may be therapeutically useful to treat gastroschisis. Accordingly, the invention includes a method of screening a candidate compound to identify a compound capable of stimulating expression of an ACLP, e.g., human ACLP, by (a) providing a cell or tissue expressing capable of expressing a ACLP, (b) contacting the cell or tissue with the candidate compound, and (c) determining the amount of expression of the ACLP by the cell. An increase in the amount of ACLP expression in the presence of the candidate compound compared to that in the absence of the candidate compound indicates that the compound stimulates expression of the ACLP.

In addition to diagnostic methods, such as described above, the present invention encompasses methods and compositions for evaluating appropriate treatment, and treatment effectiveness of pathological conditions associated with aberrant expression of ACLP. For example, the ACLP gene can be used as a probe to classify cells in terms of their level of ACLP expression, or as a source of primers for diagnostic PCR analysis in which mutations and allelic variation of ACLP can be detected.

Other features and advantages of the invention will be apparent from the following description of the preferred embodiments there and from the claims.

BRIEF DESCRIPTION OF THE DRAWING

FIG. 1A is a diagram showing a comparison of deduced open reading frames of human ACLP and mouse ACLP. The human and mouse proteins contain 1158 and 1128 amino acids, respectively. Highlighted motifs include a signal peptide (bold, underline), a 4-fold lysine- and proline-rich repeating motif (bold, italic), a discoidin-like domain (bold, italic, underline), and a region with homology to the carboxypeptidases (bold).

DETAILED DESCRIPTION

Figure 1B:
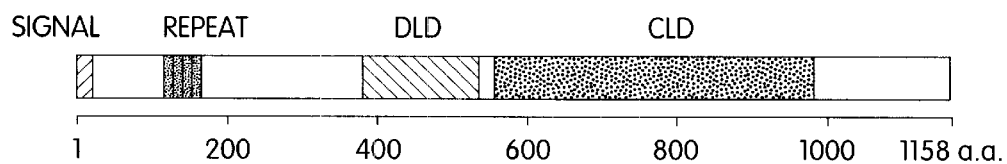
FIG. 1B is a diagram showing the location of peptide domains of human ACLP. The signal peptide sequence at the N-terminus is designated "Signal"; the 4-fold repeating motif is designated "Repeat"; the discoidin-like domain is designated "DLD"; and the region with homology to carboxypeptidases is designated "CLD".

A mutation in an ACLP-encoding nucleic acid resulting in a decrease in production of an ACLP compared to the level of ACLP production in an animal lacking the mutation has now been shown to result in the development of gastroschisis in newborn mice. The following examples describe the cloning and characterization of human ACLP and methods of diagnosing and treating gastroschisis the underlying defect of which is a genetic alteration in the ACLP genes.

EXAMPLE 1

Cloning of ACLP Genes

ACLP was identified in a screen for proteins interacting with the E47 product of the E2A gene. A recombinant E47 fusion protein (N3-SH[ALA]), containing the basic helix loop helix domain of hamster shPan-1 (amino acids 509–646, with mutations R551A, V552L, and R553A) with a heart muscle kinase recognition sequence and the FLAG epitope, was expressed and purified as described (Blanar et al., 1995, Proc. Natl. Acad. Sci. USA 92:5870–4; Blanar and Rutter, 1992, Science 256:1014–8). N3-SH[ALA] was phosphorylated by heart muscle kinase in the presence of γ-$^{32}$P-ATP and used to screen a human aorta λgt11 cDNA expression library (Clonetech) by interaction cloning (Blanar et al., 1995, Proc. Natl. Acad. Sci. USA 92:5870–4; Blanar and Rutter, 1992, Science 256:1014–8). A 1450-bp cDNA clone (ΔE2A-BP) obtained from interaction cloning was radiolabeled by random priming and used to isolate a 2786 bp cDNA clone from the same human aorta λgt11 cDNA library. Data from Northern blotting experiments revealed that the ACLP-1 RNA was about 3.9 kb in size and suggested that the 2786 bp cDNA clone was a partial cDNA clone. Additional 5' sequences of the ACLP cDNA were isolated by 5' rapid amplification of cDNA ends from human aortic smooth muscle cell RNA (Gibco-BRL). The full length sequence of the human ACLP cDNA was found to be 3935 bp and is shown in Table 1 (SEQ ID NO:1). The full length human ACLP cDNA contains an open reading frame (nucleotides 140–3613 of SEQ ID NO:1) encoding a polypeptide of 1158 amino acids. The open reading frame is preceded by a Kozak consensus translation initiation sequence, which in turn is preceded by an in frame stop codon.

The human ACLP protein has a calculated molecular mass of 130 kDa, an estimated pI of 4.8, and contains a putative signal peptide sequence. In addition, it contains an 11 amino acid lysine- and proline-rich motif repeated four times at the N-terminus, a domain with 30% amino acid identity to the slime mold adhesion protein discoidin I, and a C-terminal domain with 39% identity to carboxypeptidase E. The human ACLP gene maps to the short arm of chromosome 7 (between D7S478 amd D7S519).

The sequence of the human ACLP cDNA (GENBANK™ accession number AF053944) was compared to sequences present in GENBANK™ databases. A 3' portion of ACLP CDNA was found to share homology with the sequence of a cDNA encoding mouse adipocyte enhancer binding protein 1 (AEBP1; He et al., 1995, Nature 378:92). AEBP1 was originally identified as a 2.5 kb cDNA that hybridized to a 4 kb band on Northern blot analysis, and was predicted to encode a 719 amino acid, 79 kDa protein.

To isolate mouse ACLP cDNA (GENBANK™ accession number AF053943), first strand cDNA from C2C12 mouse myoblast total RNA was synthesized by reverse transcription with the primer 5' ATCTGGTTGTCCTCAAT 3' (SEQ ID NO:4). The nested primer 5' TGACTCCATCCCAATAG 3' (SEQ ID NO:5) and the anchor primer included in the kit for 5' rapid amplification of cDNA ends was then amplified to produce a product of approximately 1400 bp in size. This product was sequenced using standard methods.

The entire open reading frame of mouse ACLP was then amplified from C2C12 RNA by reverse transcription PCR (EXPANDLONG™ Template PCR System, Boehringer Mannheim, Indianapolis, Ind.). The human and mouse clones were sequenced by the dideoxy nucleotide chain termination method using a combination of Sequenase Version 2.0 (Amersham, Arlington Heights, Ill.), the Thermo Sequenase $^{33}$P terminator cycle sequencing kit (Amersham), and the Thermo Sequenase fluorescent-labeled cycle sequencing kit with 7-deaza-GTP (Amersham) on a Licor (Lincoln, Nebr.) apparatus.

Sequencing of the 3633 bp mouse ACLP cDNA fragment, revealed that it encoded an open reading frame (1128 amino acids) similar to that of the full-length human ACLP cDNA, indicating that it is the mouse ACLP homologue. A comparison of the human and mouse ACLP amino acid sequences is shown in FIG. 1A. Overall, the two proteins are 85% identical and 90% similar.

Figure 2A:
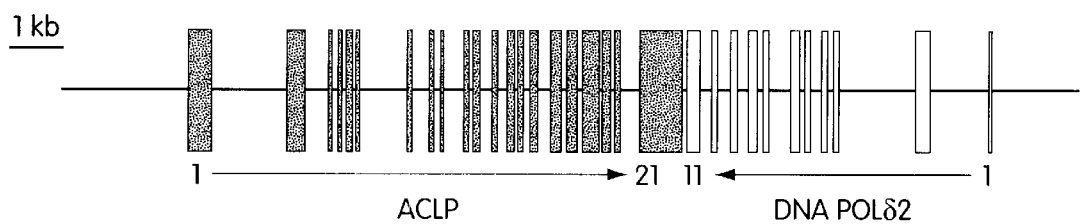
FIG. 2A is a diagram of mouse genomic DNA showing a map of the mouse ACLP gene and neighboring DNA polymerase delta small subunit gene.
Figure 2B:
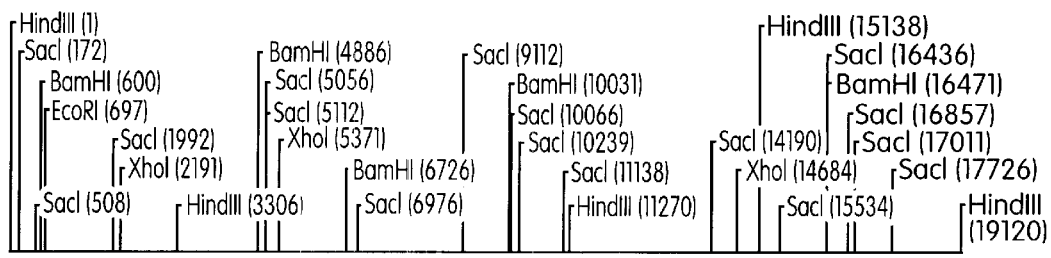
FIG. 2B is a diagram of a restriction map of genomic DNA containing the mouse ACLP gene and neighboring DNA polymerase delta small subunit gene.

EXAMPLE 2
Identification of a Promoter-Enhancer Sequence Associated with the ACLP Gene To identify genomic sequences that mediate tissue specific and developmental expression pattern of the ACLP gene, a region of genomic DNA adjoining the 5' end of the mouse ACLP coding sequences was isolated (FIGS. 2A and 2B). Portions of this genomic DNA were then used in reporter transfection assays to determine their ability to direct expression of a reporter gene in transfection assays. ACLP promoter/enhancer DNA was cloned into the pGL2 Basic vector (Stratagene) and transfected into rat aortic smooth muscle cells (RASMC) to measure promoter activity. Using this assay, a region containing an ACLP promoter/enhancer sequence was identified and is shown in Table 3 (SEQ ID NO:3). ACLP promoter/enhancer DNA was found to have transcriptional activity both in vitro (using cultured cells) and in vivo (in a transgenic mouse).

EXAMPLE 3
Generation and Characterization of Antibodies to ACLP Peptides

A carboxy terminal fragment of mouse ACLP was expressed in bacteria, purified, and used as an immunogen to raise antibodies in rabbits.

To produce a polyclonal anti-ACLP antibody, a BamHI-EcoRI fragment of mouse ACLP (encoding amino acids 615–1128) was subcloned into the pRSET C bacterial expression vector (Invitrogen), and the resulting plasmid was transformed into BL21(DE3)pLysS-competent bacteria (Stratagene). Protein expression was induced with 1 mM isopropyl β-D-thiogalactopyranoside for 3 h. Bacteria were sonicated in lysis buffer (50 mM $NaH_2PO_4$, 10 mM Tris, pH 8, 100 mM NaCl) containing the protease inhibitors aprotinin, leupeptin, and phenylmethylsulfonyl fluoride. Lysates were clarified by centrifugation at 10,000 g for 15 min, and the pellet was resuspended in lysis buffer supplemented with 8 M urea. His-tagged proteins were purified with Talon resin (Clontech) and eluted in lysis buffer containing 8 M urea and 100 mM ethylene diamine tetraacetic acid. Proteins were dialyzed against water and measured with the Bio-Rad (Hercules, Calif.) protein assay reagent. 100 μg of the purified protein was used to immunize New Zealand white rabbits. Antiserum was collected, titered against the recombinant protein, and used for immunoblot analysis. Specificity of the antiserum was determined by using preimmune serum and by competition with a recombinant protein. The same methods are used to raise antibodies to human ACLP. The rabbit antisera raised against a portion of mouse ACLP was found to crossreact with human ACLP.

Protein extracts from cultured cells were prepared for Western blotting in extraction buffer (25 mM Tris, pH 7.4, 50 mM NaCl, 0.5% sodium deoxycholate, 2% Nonidet P-40, and 0.2% sodium dodecyl sulfate) containing the protease inhibitors aprotinin, leupeptin, and phenylmethylsulfonyl fluoride. To obtain proteins from mouse tissues, individual organs were homogenized in 25 mM Tris, pH 7.5, 50 mM NaCl, and 10 mM ethylene diamine tetraacetic acid containing protease inhibitors (Complete, Boehringer Mannheim). Proteins were measured with the BCA protein assay kit (Pierce, Rockford, Ill.). After 50 μg aliquots had been resolved on 6% sodium dodecyl sulfate-polyacrylamide gels (18), proteins were transferred electrophoretically to nitrocellulose membranes (Schleicher and Schuell, Keene, N.H.) in 48 mM Tris, pH 8.3, 39 mM glycine, 0.037% sodium dodecyl sulfate, and 20% methanol transfer buffer. Blots were equilibrated with 25 mM Tris, pH 8, 125 mM NaCl, and 0.1% Tween 20 and blocked in the same solution containing 4% nonfat dry milk. Blots were incubated with anti-ACLP serum diluted 1:1000 and then horseradish peroxidase-conjugated goat anti-rabbit serum diluted 1:4000. Membranes were processed with an enhanced chemiluminescence reagent (ECL reagent, NEN, Boston, Mass.) and exposed to film.

By Western blot analysis, this antibody detected a single band corresponding to a protein with an apparent mobility of approximately 175 kDa in mouse aortic smooth muscle cells (MASMC) extracts. This protein showed a similar migration to a protein generated by transcription and translation in vitro of a mouse ACLP cDNA clone, providing additional evidence that the isolated human and mouse cDNA clones encode full-length ACLP.

Monoclonal antibodies can be obtained using full-length human or mouse ACLP or fragments thereof using standard methods, e.g., the process described by Milstein and Kohler, 1975, Nature 256:495–97, or as modified by Gerhard, 1980, Monoclonal Antibodies, Plenum Press, pages 370–371. Hybridomas are screened to identify those producing antibodies that are specific for an ACLP. Preferably, the antibody will have an affinity of at least about $10^8$ liters/mole and more preferably, an affinity of at least about $10^9$ liters/mole.

EXAMPLE 4
Subcellular Localization and Tissue Localization of ACLP Proteins To assess the subcellular localization of ACLP, a mouse ACLP expression construct was generated with a c-myc epitope at the C-terminus. The myc epitope was placed at the C-terminus to avoid interference with signal peptide-mediated processes, e.g., ACLP secretion mechanisms. To construct a c-myc-tagged ACLP expression plasmid (pcDNA3.1/ACLP-Myc-His), the open reading frame of mouse ACLP was amplified with the Expand Long Template PCR System (Boehringer Mannheim). A 5' primer containing an EcoRI site (5' CGGAATTCAGTCCCTGCT-CAAGCCCG 3'; SEQ ID NO:6) and a 3' primer containing a HindIII site (5' CGAAGCTTGAAGTCCCCAAAGT-TCACTG 3'; SEQ ID NO:7) was used, which resulted in the deletion of the endogenous termination codon in the PCR product. The PCR product was then digested with EcoRI and HindIII restriction enzymes and ligated into the EcoRI and HindIII sites of pcDNA3.1(−)/Myc-His A (Invitrogen). Cells were transfected transiently with pcDNA3.1/ACLP-Myc-His by the DEAE-dextran method with minor modifications (Tan et al., Kidney International 46:690, 1994). Twenty-four hours after transfection, cells were trypsinized and plated onto chamber slides (Nunc, Naperville, Ill.) and grown for an additional 24 h. Cells were fixed with 4% paraformaldehyde in phosphate-buffered saline and immunostained using standard methods.

Amonoclonal anti-c-myc primary antibody (9E10 Ab-1, Oncogene Research Products, Cambridge, Mass.) and a rhodamine-conjugated goat anti-mouse IgG secondary antibody were used to immunostain the cells. Nuclei were counterstained with Hoechst 33258 (1 μg/ml) and visualized with a fluorescence microscope.

RASMC and A7r5 cells both exhibited strong membrane-associated or cytoplasmic staining. Staining was most intense in the perinuclear region and was not observed in the nucleus. Various other tissues were examined for the presence of ACLP mRNA and protein. Gene expression studies confirmed expression in aortic smooth muscle cells, and levels of ACLP mRNA were found to be high in the whole aorta (including adventitia) compared to most other tissue types tested, e.g., heart, brain, stomach, thymus, and liver. ACLP message was also detectable in colon and kidney tissue.

To examine expression of ACLP, extracts from mouse tissues were subjected to Western blot analysis using anti-ACLP sera. ACLP was strongly expressed in the mouse aorta (without adventitia) but not in the adventitia, heart, liver, skeletal muscle, or kidney. The presence of ACLP mRNA in the kidney (but absence of protein) indicates that the level of ACLP in the cells is regulated at the level of translation of ACLP mRNA into polypeptide.

To identify cell types expressing ACLP in an adult animal, in situ hybridization was performed on adult rat aorta and skeletal muscle using known methods. Adult male Sprague-Dawley rats were perfused with 4% paraformaldehyde and their organs were removed and sectioned. ACLP mRNA was detected with a [$^{35}$S] UTP-labeled antisense riboprobe synthesized with SP6 RNA polymerase from a linearized 0.7 kb fragment of ACLP cDNA. As a control, a sense RNA probe was synthesized with T7 RNA polymerase from a linearized ACLP cDNA fragment. The antisense riboprobe detected specific ACLP expression in the smooth muscle cells of the aorta, whereas the control (sense) probe did not. Neither the sense nor the antisense probe hybridized to skeletal muscle cells.

EXAMPLE 5
ACLP Expression in Smooth Muscle Cell Differentiation

ACLP protein expression was examined during vascular smooth muscle cell growth and differentiation. RASMC and MASMC were isolated from the thoracic aortas of adult male Sprague-Dawley rats and C57Bl/6 mice using standard methods. Human aortic smooth muscle cells (HASMC) were purchased from Clonetics (San Diego, Calif.), and rat A7r5 smooth muscle cells and C2C12 mouse myoblasts were purchased from the American Type Culture Collection (Rockville, Md.). Mouse neural crest cells (Monc-1 cells) were cultured on fibronectin-coated plates. RASMC, MASMC, and A7r5 cells were cultured in Dulbecco's modified Eagle's medium with 3.7 g/liter glucose (Gibco-BRL, Gaithersburg, MD) supplemented with 10% fetal bovine serum (Hyclone, Logan, UT), 4 mML-glutamine, 100 µg/ml streptomycin, 100 units/ml penicillin, and 10 mM HEPES (pH 7.4). C2C12 cells were grown in Dulbecco's modified Eagle's medium supplemented with 15% fetal bovine serum, 4 mM L-glutamine, 100 µg/ml streptomycin, and 100 units/ml penicillin. HASMC were cultured in M199 medium (Gibco) supplemented with 20% fetal bovine serum, 4 mM L-glutamine, 100 µg/ml streptomycin, and 100 units/ml penicillin. Cells were grown at 37° C. in a humidified incubator containing 5% $CO_2$. MASMC were cultured for 3 days in 0.4% calf serum containing medium that induces quiescence. RNA and protein extracts were then prepared from the cells and analyzed.

The amount of ACLP mRNA was higher (about 2-fold) in serum-starved (quiescent) MASMC than in control cells (normal proliferating MASMC). In RASMC, ACLP mRNA was approximately 3-fold more abundant in quiescent cells than in their actively proliferating counterparts. ACLP protein was also elevated in quiescent MASMC.

ACLP expression was examined in an in vitro system for differentiating smooth muscle cells from a Monc-1 cell line, a mouse line derived from the neural crest. Monc-1 cells differentiate into smooth muscle cells when tissue culture medium supplemented with chick embryo extract is replaced with differentiation medium. To examine ACLP expression during the transition of undifferentiated Monc-1 cells to smooth muscle, the time course of ACLP expression was measured. ACLP mRNA was nearly undetectable in undifferentiated Monc-1 cells. As the cells differentiated, however, ACLP expression increased until it became marked at days 4 and 6 after the start of differentiation. Under these conditions, induction of ACLP appeared to lag behind that of smooth muscle α-actin, a marker for smooth muscle cells. To compare the level of ACLP protein in cells treated similarly, protein extracts were prepared from undifferentiated Monc-1 cells and from cells allowed to differentiate for 6 days. ACLP protein was not detectable in undifferentiated Monc-1 cells but was expressed highly (day 6) under conditions that promote Monc-1 cell differentiation into smooth muscle cells. The abundance of ACLP protein in these cells was similar to that in MASMC.

As is described below, the Monc-1 cells (and other cells expressing ACLP) can be used to screen for compounds that stimulate a therapeutic increase in ACLP production (e.g., during cell differentiation and/or fetal development).

EXAMPLE 6
Genetically-altered Animals

An ACLP deficient animal, e.g., an ACLP knockout mouse, is produced as follows.

Figure 3:
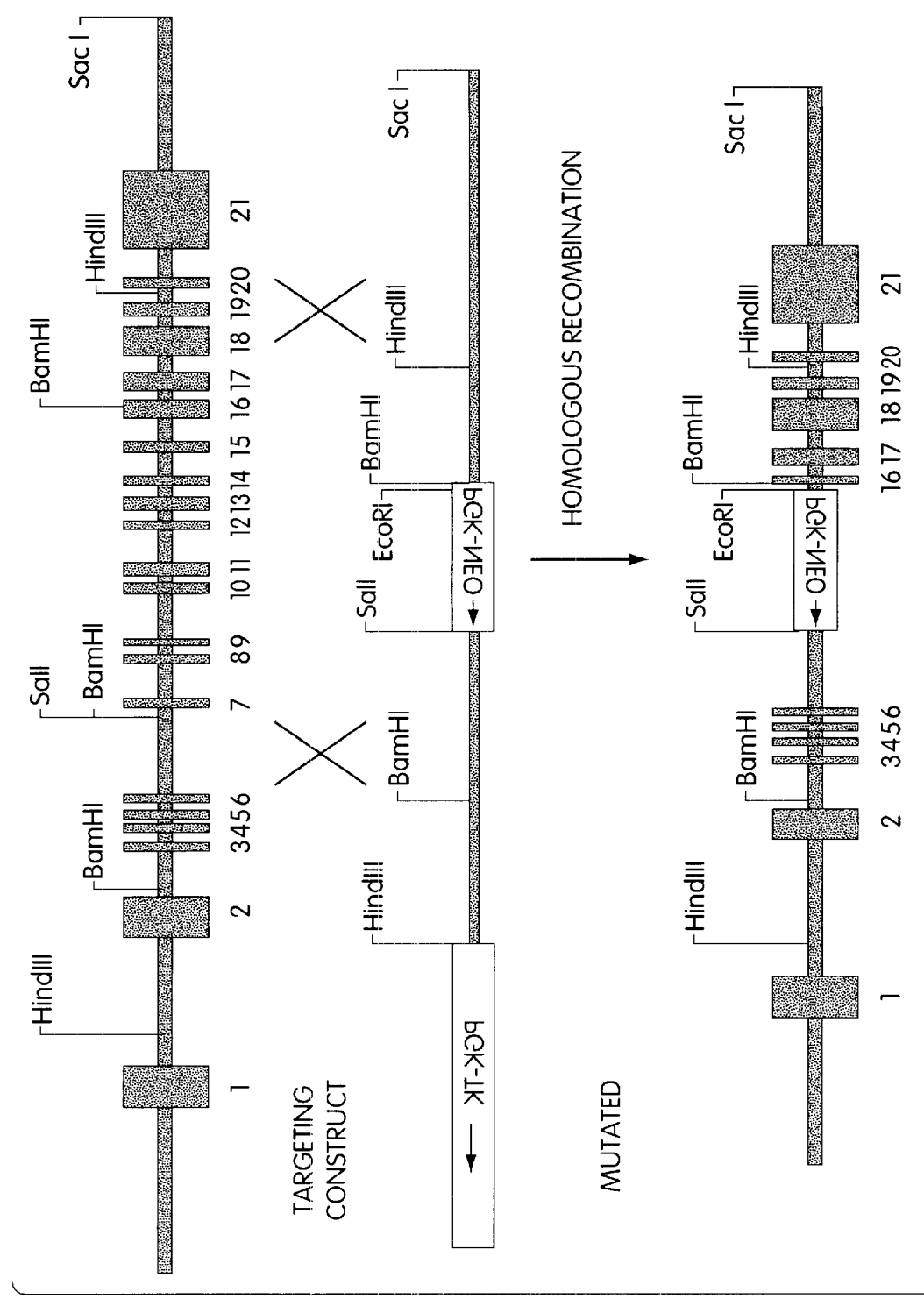
FIG. 3 is a diagram showing a map of the targeting construct used to make an ACLP knockout mouse.

The targeting construct was made by deleting exons, e.g., 7–15 of the mouse ACLP gene (see FIG. 3). A SalI-BamHI fragment of the ACLP gene was replaced with pPGK-neo to generate the targeting construct.

The linearized targeting construct (shown in FIG. 3) was transfected into murine D3 embryonic stem (ES) cells, and a clone with the correct homologous recombination (yielding the appropriately disrupted ACLP gene shown in FIG. 3) injected into blastocysts and used to generate ACLP chimeric mice using standard methods. The chimeric mice were bred with wild type mice to generate ACLP-mutated heterozyous mice. ACLP-mutated heterozygous mice were born normal. To generate an ACLP knockout mouse (i.e., homozygous for the ACLP mutation), the heterozygous mice were mated. The genotype of newborn mice was evaluated at 3 weeks. Out of 205 live pups, 74 were found to have the wild type ACLP gene, 113 were found to be heterozygotes, and 18 were found to be homozygous for the ACLP null mutation, i.e., ACLP knockout mice. These data indicate that many of the knockout mice died before or immediately after birth.

The phenotype of ACLP knockout mice was evaluated during development. Cesarean sections were performed to obtain embryos at 18.5 embryonic days (El8.5). ACLP-knockout mice were found to have an abdominal defect with extrusion of abdominal organs, whereas the wild type mice were normal.

The progress of the development of gastroschisis is evaluated by mating heterozygous ACLP-mutant mice and obtaining embryos at various time points, e.g., E18.5, E16.5, E12.5, E10.5, and E8.5. Embryos are examined at both gross and microscopic levels. Histological evaluation of embryonic tissue, e.g., to follow the formation of the omphalomesenteric arteries, is used to determine the incidence and time of development of gastroschisis.

ACLP-deficient animals can be used to screen for compounds to treat or prevent the development of gastroschisis. To determine whether a given compound prevents or reduces the development of gastroschisis in developing embryos, the compound is administered to the pregnant animal (e.g., systemically, in utero, or directly to an embryo itself) and the embryos examined as described above. For example, a nucleic acid encoding a full length wild type ACLP gene (or an ACLP gene which may differ from the wild type sequence but still retains ACLP function) can be tested to evaluate the effect of such gene therapy on the development of gastroschisis. A reduction in the severity of gastroschisis in treated embryos compared to untreated embryos indicates that the compound or gene therapy approach to treatment of gastroschisis is clinically beneficial.

ACLP deficient mice and ACLP deficient cell lines derived from such mice are useful in determining the etiology of gastroschisis and screening for therapeutic compositions.

EXAMPLE 7
Diagnosis of Disorders Associated with Altered Levels of ACLP Expression or Activity The data described herein indicates that an ACLP mutation (e.g., in ACLP coding or regulatory sequences) is involved in the development of gastroschisis. Thus, individuals (e.g., those with a family history of the disease) can be tested for the presence of a mutated ACLP gene which may contribute to the development of gastroschisis in children of an individual harboring a mutated gene. Detection of such a mutation will permit appropriate genetic counseling of those individuals regarding the risks associated with pregnancy. In addition, such testing can be used to identify individuals with subclinical gastroschisis or other related gastrointestinal abnormalities. Prenatal testing may be carried out to determine whether a developing fetus is at risk of developing gastroschisis. Although gastroschisis may be detected at approximately the second trimester of pregnancy by conventional prenatal ultrasound testing, early detection of a genetic abnormality permits early intervention, including genetic therapy, which may prevent the development of the condition or reduce its severity.

Analysis can be carried out on any suitable genomic DNA sample (e.g., maternal tissue and/or fetal tissue) to be tested. Typically, a blood sample or a sample of placental or umbilical cord cells is tested. A sample of fetal cells can be obtained by amniocentesis or chorionic villi sampling.

Standard genetic diagnostic methods are used to detect a mutation in the ACLP gene. For example, PCR (polymerase chain reaction) is used to identify the presence of a deletion, addition, or substitution of one or more nucleotides within any one of the exons of ACLP. Following the PCR reaction, the PCR product can be analyzed by methods as described above, such as the heteroduplex detection technique based upon that of White et al., 1992, Genomics 12:301–306, or by techniques such as cleavage of RNA-DNA hybrids using RNase A (Myers et al., 1985, Science 230:1242–1246); single-stranded conformation polymorphism (SSCP) analysis (Orita et al., 1989, Genomics 10:298–299); and denaturing gradient gel electrophoresis (DGGE; Myers et al., 1987, Methods Enzymol. 155:501–527). PCR may be carried out using a primer which adds a G+C-rich sequence (termed a "GC-clamp") to one end of the PCR product, thus improving the sensitivity of the subsequent DGGE procedure (Sheffield et al., 1989, Proc. Natl. Acad. Sci. USA 86:232–236). If the particular mutation present in the patient's family is known to have removed or added a restriction site, or to have significantly increased or decreased the length of a particular restriction fragment, a protocol based upon restriction fragment length polymorphism (RFLP) analysis (perhaps combined with PCR) can be used to identify the genetic defect.

In addition to evaluating genomic DNA of a patient, an ACLP defect can be detected by evaluating an ACLP gene product. Unlike genomic DNA-based diagnostic methods, this approach permits detection of defects resulting in a decrease in the level of expression of an ACLP gene (i.e., a defect which does not involve mutations in the coding sequence itself). In addition to detection of a gene product, gene expression is also measured using mRNA-based methods, such as Northern blots and in situ hybridization (using a nucleic acid probe derived from the relevant cDNA), and quantitative PCR.

An ACLP gene product can be tested for abnormalities, e.g., differences in the level of expression compared to wild type ACLP, truncation of an ACLP gene product, or deletion of a portion of an ACLP gene product. Deletion ACLP mutants, e.g., those characterized by the loss of an ACLP epitope, can be detected using an ACLP-specific antibody. Western blotting and Northern blotting techniques are used to quantitate the amount of expression of a ACLP in the tissue of interest. For example, an individual who is heterozygous for a genetic defect affecting level of expression of ACLP may be diagnosed by detecting reduction in the level of expression of this gene in such a hybridization or antibody-based assay, and an individual who is homozygous may be identified by detection of a comparatively lower level of expression.

The diagnostic method of the invention is carried out by measuring ACLP gene expression in a tissue, e.g, a biopsy, or in a bodily fluid, e.g., blood or plasma. Detection of expression and determination of the level of gene expression is measured using methods known in the art, e.g., in situ hybridization, Northern blot analysis, or Western blot analysis using ACLP-specific monoclonal or polyclonal antibodies. An decrease in the level of ACLP expression per cell in the test sample of tissue compared to the level per cell in control tissue indicates that the patient has gastroschisis, is predisposed to developing gastroschisis, or is a carrier of a genetic defect associated with gastroschisis.

The diagnostic procedures described above are useful to identify patients in need of therapeutic intervention to reduce the severity of or prevent the development of gastroschisis.

EXAMPLE 8
Treatment of Disorders Associated with Altered Levels of ACLP Expression or Activity Gene therapy may be carried out by administering to a patient a nucleic acid encoding a therapeutic polypeptide, e.g., an ACLP or fragment thereof, by standard vectors and/or gene delivery systems. Suitable gene delivery systems may include liposomes, receptor-mediated delivery systems, naked DNA, and viral vectors such as herpes viruses, retroviruses, adenoviruses and adeno-associated viruses, among others.

In addition to a gene delivery system as described above, the therapeutic composition may include a pharmaceutically acceptable carrier, e.g., a biologically compatible vehicle such as physiological saline, suitable for administration to an animal. A therapeutically effective amount of a compound is an amount which is capable of producing a medically desirable result in a treated animal, e.g., a reduction in the severity of gastroschisis or the prevention of the development of gastroschisis (e.g., in a fetus).

Parenteral administration, such as intravenous, subcutaneous, intramuscular, and intraperitoneal delivery routes, may be used to deliver the compound. Dosage for any one patient depends upon many factors, including the patient's size, body surface area, age, the particular compound to be administered, sex, time and route of administration, general health, and other drugs being administered concurrently. Dosage of the compound to be administered will vary. A preferred dosage for intravenous administration of nucleic acids is from approximately $10^6$ to $10^{22}$ copies of the nucleic acid molecule. Compounds, including therapeutic nucleic acids, may be administered locally through the uterine wall to the developing fetus using known methods.

ACLPs may be similarly administered, e.g., locally or systemically, e.g., intravenously, in a pharmaceutically acceptable carrier such as physiological saline. Standard methods for intracellular delivery of peptides can be used, e.g. packaged in liposomes. Such methods are well known to those of ordinary skill in the art. It is expected that an intravenous dosage of approximately 1 to 100 µmoles of the polypeptide of the invention would be administered per kg of body weight per day. The compositions of the invention are useful for parenteral administration, such as intravenous, subcutaneous, intramuscular, and intraperitoneal.

ACLP encoding DNA is be introduced into target cells of the patient by standard vectors, e.g., a vector which contains DNA encoding an ACLP operably linked to an ACLP promoter/enhancer sequence. Suitable gene delivery systems may include liposomes, receptor-mediated delivery systems, naked DNA, and viral vectors such as herpes viruses, retroviruses, and adenoviruses, among others. ACLP DNA under the control of a strong constitutive promoter may be administered locally using an adenovirus delivery system.

Drugs which stimulate an endogenous ACLP promoter may also be administered as described above to increase the level of expression ACLP in patients in which the underlying clinical defect is a pathologically low level of ACLP production.

EXAMPLE 9

Identification of Compounds that Alter ACLP Expression or Activity

ACLP knockout mice have the clinical manifestations of gastroschisis. Compositions that ameliorate the symptoms of gastroschisis or prevent the development of gastroschisis in a developing fetus can be identified using ACLP knockout mice. A test compound is administered to an ACLP knockout mouse. As a control, the compound is administered to a normal wild type mouse (preferably with the same genetic background as the ACLP knockout mouse). A reduction in the severity of gastroschisis in ACLP knockout mice treated with the test compound compared to control ACLP mice which have not been exposed to the test compound is an indication that the test compound is capable of ameliorating the symptoms of or preventing the development of gastroschisis.

Compounds can also be screened by contacting cells in vitro, e.g., VASMC, MASMC, RASMC, Monc-1 cells, or cells derived from an ACLP knockout mouse or from an animal or patient with gastroschisis, with a candidate compound and measuring the level of ACLP expression (or activity) in the cells. An increase in cellular ACLP expression (compared to the level of expression in the absence of a test compound) indicates that the compound is clinically useful to prevent or treat gastroschisis in which the underlying defect is pathological reduction in the level of ACLP production.

Other embodiments are within the following claims.

---

What is claimed is:

1. An isolated nucleic acid molecule comprising a nucleotide sequence, said nucleotide sequence encoding a polypeptide comprising an amino acid sequence which is at least 87% identical to SEQ ID NO:2 over the entire length of SEQ ID NO: 2 and which amino acid sequence comprises
   (a) a discoidin domain comprising amino acids 385–540 of SEQ ID NO:2;
   (b) a lysine-rich/proline-rich domain comprising amino acids 117–164 of SEQ ID NO:2; and
   (c) a carboxypeptidase domain comprising amino acids 562–969 of SEQ ID NO:2, wherein an amino acid substitution in said polypeptide is conservative with respect to SEQ ID NO:2 and wherein the absence of said polypeptide is associated with gastroschisis.

2. The nucleic acid molecule of claim 1, wherein said nucleic acid molecule is operably linked to a regulatory sequence for expression of said nucleic acid molecule, said regulatory sequence comprising a promoter.

3. The nucleic acid molecule of claim 1, wherein said nucleic acid molecule comprises nucleotides 1292 to 1759 of SEQ ID NO: 1.

4. The nucleic acid molecule of claim 1, wherein said nucleic acid molecule comprises nucleotides 1823 to 3046 of SEQ ID NO: 1.

5. The nucleic acid molecule of claim 1, wherein said amino acid sequence is at least 90% identical to the sequence of SEQ ID NO: 2 over the entire length of SEQ ID NO:2.

6. The nucleic acid molecule of claim 1, wherein said amino acid sequence is at least 95% identical to the sequence of SEQ ID NO: 2 over the entire length of SEQ ID NO:2.

7. The nucleic acid molecule of claim 1, wherein said amino acid sequence is at least 99% identical to the sequence of SEQ ID NO: 2 over the entire length of SEQ ID NO:2.

8. An isolated nucleic acid molecule, wherein said nucleic acid molecule comprises the nucleotides 140–3613, inclusive, of SEQ ID NO:1.

9. A cell comprising the nucleic acid molecule of claim 8.

10. A method of making a polypeptide comprising the amino acid sequence of SEQ ID NO:2, comprising (a) providing the cell of claim 9, and (b) culturing it under conditions permitting expression of said nucleic acid molecule, wherein said polypeptide is produced.

11. An isolated nucleic acid molecule comprising a a nucleotide sequence selected from the group consisting of (a) nucleotides 140–3613, inclusive, of SEQ ID NO:1, and (b) the nucleotide sequence of the complement of nucleotides 140–3613, inclusive of SEQ ID NO:1.

* * * * *

UNITED STATES PATENT AND TRADEMARK OFFICE
CERTIFICATE OF CORRECTION

PATENT NO.    : 6,468,766 B1
DATED         : October 22, 2002
INVENTOR(S)   : Mu-En Lee, Matthew D. Layne and Shaw-Fang Yet It is certified that error appears in the above-identified patent and that said Letters Patent is hereby corrected as shown below:

<u>Column 1,</u>
Line 16, after "grant", delete "numbers RO1GM", and insert -- number GM53249 --.

Signed and Sealed this

Fifth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,468,766 B1  
APPLICATION NO. : 09/060482  
DATED : October 22, 2002  
INVENTOR(S) : Lee et al.

Page 1 of 1

It is certified that error appears in the above-identified patent and that said Letters Patent is hereby corrected as shown below:

In the Specification:

At Column 1, Line number 15, please delete the paragraph labeled "STATEMENT AS TO FEDERALLY SPONSORED RESEARCH" and replace it with the following paragraph:
This invention was made with government support under GM053249 awarded by the National Institutes of Health. The government has certain rights in the invention.

Signed and Sealed this  
Nineteenth Day of August, 2025

Coke Morgan Stewart  
*Acting Director of the United States Patent and Trademark Office*

SEQUENCE LISTING

<160> NUMBER OF SEQ ID NOS: 8

<210> SEQ ID NO 1
<211> LENGTH: 3935
<212> TYPE: DNA
<213> ORGANISM: Homo sapiens
<220> FEATURE:
<221> NAME/KEY: CDS
<222> LOCATION: (140)...(3613)

<400> SEQUENCE: 1

```
tccctcgctc acccatcct ctctcccgcc ccttcctgga ttccctcacc cgtctcgatc      60
ccctctccgc cctttcccag agacccagag cccctgaccc cccgcgccct ccccggagcc    120
ccccgcgcgt gccgcggcc atg gcg gcc gtg cgc ggg gcg ccc ctg ctc agc    172
                     Met Ala Ala Val Arg Gly Ala Pro Leu Leu Ser
                      1               5                       10 tgc ctc ctg gcg ttg ctg gcc ctg tgc cct gga ggg cgc ccg cag acg    220
Cys Leu Leu Ala Leu Leu Ala Leu Cys Pro Gly Gly Arg Pro Gln Thr
            15                  20                      25 gtg ctg acc gac gac gag atc gag gag ttc ctc gag ggc ttc ctg tca    268
Val Leu Thr Asp Asp Glu Ile Glu Glu Phe Leu Glu Gly Phe Leu Ser
        30                      35                      40 gag cta gaa cct gag ccc cgg gag gac gac gtg gag gcc ccg ccg cct    316
Glu Leu Glu Pro Glu Pro Arg Glu Asp Asp Val Glu Ala Pro Pro Pro
    45                      50                      55 ccc gag ccc acc ccg cgg gtc cga aaa gcc cag gcg ggg ggc aag cca    364
Pro Glu Pro Thr Pro Arg Val Arg Lys Ala Gln Ala Gly Gly Lys Pro
60                      65                      70                  75 ggg aag cgg cca ggg acg gcc gca gaa gtg cct ccg gaa aag acc aaa    412
Gly Lys Arg Pro Gly Thr Ala Ala Glu Val Pro Pro Glu Lys Thr Lys
```

|  |  |
|---|---|
| gac aaa ggg aag aaa ggc aag aaa gac aaa ggc ccc aag gtg ccc aag<br>Asp Lys Gly Lys Lys Gly Lys Lys Asp Lys Gly Pro Lys Val Pro Lys<br>                95                          100                    105 | 460 |
| gag tcc ttg gag ggg tcc ccc agg ccg ccc aag aag ggg aag gag aag<br>Glu Ser Leu Glu Gly Ser Pro Arg Pro Pro Lys Lys Gly Lys Glu Lys<br>        110                      115                    120 | 508 |
| cca ccc aag gcc acc aag aag ccc aag gag aag cca cct aag gcc acc<br>Pro Pro Lys Ala Thr Lys Lys Pro Lys Glu Lys Pro Pro Lys Ala Thr<br>125                      130                    135 | 556 |
| aag aag ccc aag gag gag cca ccc aag gcc acc aag aag ccc aaa gag<br>Lys Lys Pro Lys Glu Glu Pro Pro Lys Ala Thr Lys Lys Pro Lys Glu<br>140                  145                    150                    155 | 604 |
| aag cca ccc aag gcc acc aag aag ccc ccg tca ggg aag agg ccc ccc<br>Lys Pro Pro Lys Ala Thr Lys Lys Pro Pro Ser Gly Lys Arg Pro Pro<br>                160                        165                    170 | 652 |
| att ctg gct ccc tca gaa acc ctg gag tgg cca ctg ccc cca ccc ccc<br>Ile Leu Ala Pro Ser Glu Thr Leu Glu Trp Pro Leu Pro Pro Pro Pro<br>                  175                      180                    185 | 700 |
| agc cct ggc ccc gag gag cta ccc cag gag gga ggg gcg ccc ctc tca<br>Ser Pro Gly Pro Glu Glu Leu Pro Gln Glu Gly Gly Ala Pro Leu Ser<br>        190                      195                    200 | 748 |
| aat aac tgg cag aat cca gga gag gag acc cat gtg gag gca cag gag<br>Asn Asn Trp Gln Asn Pro Gly Glu Glu Thr His Val Glu Ala Gln Glu<br>                205                      210                    215 | 796 |
| cac cag cct gag ccg gag gag gag acc gag caa ccc aca ctg gac tac<br>His Gln Pro Glu Pro Glu Glu Glu Thr Glu Gln Pro Thr Leu Asp Tyr<br>220                      225                    230                    235 | 844 |
| aat gac cag atc gag agg gag gac tat gag gac ttt gag tac att cgg<br>Asn Asp Gln Ile Glu Arg Glu Asp Tyr Glu Asp Phe Glu Tyr Ile Arg<br>                240                      245                    250 | 892 |
| cgc cag aag caa ccc agg cca ccc cca agc aga agg agg agg ccc gag<br>Arg Gln Lys Gln Pro Arg Pro Pro Pro Ser Arg Arg Arg Arg Pro Glu<br>                    255                      260                    265 | 940 |
| cgg gtc tgg cca gag ccc cct gag gag aag gcc ccg gcc cca gcc ccg<br>Arg Val Trp Pro Glu Pro Pro Glu Glu Lys Ala Pro Ala Pro Ala Pro<br>        270                      275                    280 | 988 |
| gag gag agg att gag cct cct gtg aag cct ctg ctg ccc ccg ctg ccc<br>Glu Glu Arg Ile Glu Pro Pro Val Lys Pro Leu Leu Pro Pro Leu Pro<br>        285                      290                    295 | 1036 |
| cct gac tat ggt gat ggt tac gtg atc ccc aac tac gat gac atg gac<br>Pro Asp Tyr Gly Asp Gly Tyr Val Ile Pro Asn Tyr Asp Asp Met Asp<br>300                      305                    310                    315 | 1084 |
| tat tac ttt ggg cct cct ccg ccc cag aag ccc gat gct gag cgc cag<br>Tyr Tyr Phe Gly Pro Pro Pro Pro Gln Lys Pro Asp Ala Glu Arg Gln<br>                320                      325                    330 | 1132 |
| acg gac gaa gag aag gag gag ctg aag aaa ccc aaa aag gag gac agc<br>Thr Asp Glu Glu Lys Glu Glu Leu Lys Lys Pro Lys Lys Glu Asp Ser<br>                335                      340                    345 | 1180 |
| agc ccc aag gag gag acc gac aag tgg gca gtg gag aag ggc aag gac<br>Ser Pro Lys Glu Glu Thr Asp Lys Trp Ala Val Glu Lys Gly Lys Asp<br>        350                      355                    360 | 1228 |
| cac aaa gag ccc cga aag ggc gag gag ttg gag gag gag tgg acg cct<br>His Lys Glu Pro Arg Lys Gly Glu Glu Leu Glu Glu Glu Trp Thr Pro<br>        365                      370                    375 | 1276 |
| acg gag aaa gtc aag tgt ccc ccc att ggg atg gag tca cac cgt att<br>Thr Glu Lys Val Lys Cys Pro Pro Ile Gly Met Glu Ser His Arg Ile<br>380                      385                    390                    395 | 1324 |
| gag gac aac cag atc cga gcc tcc tcc atg ctg cgc cac ggc ctg ggg<br>  | 1372 |

-continued

```
              Glu Asp Asn Gln Ile Arg Ala Ser Ser Met Leu Arg His Gly Leu Gly
                              400                 405                 410 gca cag cgc ggc cgg ctc aac atg cag acc ggt gcc act gag gac gac        1420
Ala Gln Arg Gly Arg Leu Asn Met Gln Thr Gly Ala Thr Glu Asp Asp
            415                 420                 425 tac tat gat ggt gcg tgg tgt gcc gag gac gat gcc agg acc cag tgg        1468
Tyr Tyr Asp Gly Ala Trp Cys Ala Glu Asp Asp Ala Arg Thr Gln Trp
            430                 435                 440 ata gag gtg gac acc agg agg act acc cgg ttc aca ggc gtc atc acc        1516
Ile Glu Val Asp Thr Arg Arg Thr Thr Arg Phe Thr Gly Val Ile Thr
        445                 450                 455 cag ggc aga gac tcc agc atc cat gac gat ttt gtg acc acc ttc ttc        1564
Gln Gly Arg Asp Ser Ser Ile His Asp Asp Phe Val Thr Thr Phe Phe
460                 465                 470                 475 gtg ggc ttc agc aat gac agc cag aca tgg gtg atg tac acc aac ggc        1612
Val Gly Phe Ser Asn Asp Ser Gln Thr Trp Val Met Tyr Thr Asn Gly
                480                 485                 490 tat gag gaa atg acc ttt cat ggg aac gtg gac aag gac aca ccc gtg        1660
Tyr Glu Glu Met Thr Phe His Gly Asn Val Asp Lys Asp Thr Pro Val
            495                 500                 505 ctg agt gag ctc cca gag ccg gtg gtg gct cgt ttc atc cgc atc tac        1708
Leu Ser Glu Leu Pro Glu Pro Val Val Ala Arg Phe Ile Arg Ile Tyr
        510                 515                 520 cca ctc acc tgg aat ggc agc ctg tgc atg cgc ctg gag gtg ctg ggg        1756
Pro Leu Thr Trp Asn Gly Ser Leu Cys Met Arg Leu Glu Val Leu Gly
525                 530                 535 tgc tct gtg gcc cct gtc tac agc tac tac gca cag aat gag gtg gtg        1804
Cys Ser Val Ala Pro Val Tyr Ser Tyr Tyr Ala Gln Asn Glu Val Val
540                 545                 550                 555 gcc acc gat gac ctg gat ttc cgg cac cac agc tac aag gac atg cgc        1852
Ala Thr Asp Asp Leu Asp Phe Arg His His Ser Tyr Lys Asp Met Arg
                560                 565                 570 cag ctc atg aag gtg gtg aac gag gag tgc ccc acc atc acc cgc act        1900
Gln Leu Met Lys Val Val Asn Glu Glu Cys Pro Thr Ile Thr Arg Thr
            575                 580                 585 tac agc ctg ggc aag agc tca cga ggc ctc aag atc tat gcc atg gag        1948
Tyr Ser Leu Gly Lys Ser Ser Arg Gly Leu Lys Ile Tyr Ala Met Glu
        590                 595                 600 atc tca gac aac cct ggg gag cat gaa ctg ggg gag ccc gag ttc cgc        1996
Ile Ser Asp Asn Pro Gly Glu His Glu Leu Gly Glu Pro Glu Phe Arg
605                 610                 615 tac act gct ggg atc cat ggc aac gag gtg ctg ggc cga gag ctg ttg        2044
Tyr Thr Ala Gly Ile His Gly Asn Glu Val Leu Gly Arg Glu Leu Leu
620                 625                 630                 635 ctg ctg ctc atg cag tac ctg tgc cga gag tac cgc gat ggg aac cca        2092
Leu Leu Leu Met Gln Tyr Leu Cys Arg Glu Tyr Arg Asp Gly Asn Pro
                640                 645                 650 cgt gtg cgc agc ctg gtg cag gac aca cgc atc cac ctg gtg ccc tca        2140
Arg Val Arg Ser Leu Val Gln Asp Thr Arg Ile His Leu Val Pro Ser
            655                 660                 665 ctg aac cct gat ggc tac gag gtg gca gcg cag atg ggc tca gag ttt        2188
Leu Asn Pro Asp Gly Tyr Glu Val Ala Ala Gln Met Gly Ser Glu Phe
        670                 675                 680 ggg aac tgg gcg ctg gga ctg tgg act gag gag ggc ttt gac atc ttt        2236
Gly Asn Trp Ala Leu Gly Leu Trp Thr Glu Glu Gly Phe Asp Ile Phe
685                 690                 695 gaa gat ttc ccg gat ctc aac tct gtg ctc tgg gga gct gag gag agg        2284
Glu Asp Phe Pro Asp Leu Asn Ser Val Leu Trp Gly Ala Glu Glu Arg
700                 705                 710                 715
```

-continued

| | |
|---|---|
| aaa tgg gtc ccc tac cgg gtc ccc aac aat aac ttg ccc atc cct gaa<br>Lys Trp Val Pro Tyr Arg Val Pro Asn Asn Asn Leu Pro Ile Pro Glu<br>    720             725             730 | 2332 |
| cgc tac ctt tcg cca gat gcc acg gta tcc acg gag gtc cgg gcc atc<br>Arg Tyr Leu Ser Pro Asp Ala Thr Val Ser Thr Glu Val Arg Ala Ile<br>        735             740             745 | 2380 |
| att gcc tgg atg gag aag aac ccc ttc gtg ctg gga gca aat ctg aac<br>Ile Ala Trp Met Glu Lys Asn Pro Phe Val Leu Gly Ala Asn Leu Asn<br>    750             755             760 | 2428 |
| ggc ggc gag cgg cta gta tcc tac ccc tac gat atg gcc cgc acg cct<br>Gly Gly Glu Arg Leu Val Ser Tyr Pro Tyr Asp Met Ala Arg Thr Pro<br>765             770             775 | 2476 |
| acc cag gag cag ctg ctg gcc gca gcc atg gca gca gcc cgg ggg gag<br>Thr Gln Glu Gln Leu Leu Ala Ala Ala Met Ala Ala Ala Arg Gly Glu<br>780             785             790             795 | 2524 |
| gat gag gac gag gtc tcc gag gcc cag gag act cca gac cac gcc atc<br>Asp Glu Asp Glu Val Ser Glu Ala Gln Glu Thr Pro Asp His Ala Ile<br>        800             805             810 | 2572 |
| ttc cgg tgg ctt gcc atc tcc ttc gcc tcc gca cac ctc acc ttg acc<br>Phe Arg Trp Leu Ala Ile Ser Phe Ala Ser Ala His Leu Thr Leu Thr<br>    815             820             825 | 2620 |
| gag ccc tac cgc gga ggc tgc caa gcc cag gac tac acc ggc ggc atg<br>Glu Pro Tyr Arg Gly Gly Cys Gln Ala Gln Asp Tyr Thr Gly Gly Met<br>830             835             840 | 2668 |
| ggc atc gtc aac ggg gcc aag tgg aac ccc cgg acc ggg act atc aat<br>Gly Ile Val Asn Gly Ala Lys Trp Asn Pro Arg Thr Gly Thr Ile Asn<br>845             850             855 | 2716 |
| gac ttc agt tac ctg cat acc aac tgc ctg gag ctc tcc ttc tac ctg<br>Asp Phe Ser Tyr Leu His Thr Asn Cys Leu Glu Leu Ser Phe Tyr Leu<br>860             865             870             875 | 2764 |
| ggc tgt gac aag ttc cct cat gag agt gag ctg ccc cgc gag tgg gag<br>Gly Cys Asp Lys Phe Pro His Glu Ser Glu Leu Pro Arg Glu Trp Glu<br>        880             885             890 | 2812 |
| aac aac aag gag gcg ctg ctc acc ttc atg gag cag gtg cac cgc ggc<br>Asn Asn Lys Glu Ala Leu Leu Thr Phe Met Glu Gln Val His Arg Gly<br>    895             900             905 | 2860 |
| att aag ggg gtg gtg acg gac gag caa ggc atc ccc att gcc aac gcc<br>Ile Lys Gly Val Val Thr Asp Glu Gln Gly Ile Pro Ile Ala Asn Ala<br>910             915             920 | 2908 |
| acc atc tct gtg agt ggc att aat cac ggc gtg aag aca gcc agt ggt<br>Thr Ile Ser Val Ser Gly Ile Asn His Gly Val Lys Thr Ala Ser Gly<br>925             930             935 | 2956 |
| ggt gat tac tgg cga atc ttg aac ccg ggt gag tac cgc gtg aca gcc<br>Gly Asp Tyr Trp Arg Ile Leu Asn Pro Gly Glu Tyr Arg Val Thr Ala<br>940             945             950             955 | 3004 |
| cac gcg gag ggc tac acc ccg agc gcc aag acc tgc aat gtt gac tat<br>His Ala Glu Gly Tyr Thr Pro Ser Ala Lys Thr Cys Asn Val Asp Tyr<br>        960             965             970 | 3052 |
| gac atc ggg gcc act cag tgc aac ttc atc ctg gct cgc tcc aac tgg<br>Asp Ile Gly Ala Thr Gln Cys Asn Phe Ile Leu Ala Arg Ser Asn Trp<br>    975             980             985 | 3100 |
| aag cgc atc cgg gag atc atg gcc atg aac ggg aac cgg cct atc cca<br>Lys Arg Ile Arg Glu Ile Met Ala Met Asn Gly Asn Arg Pro Ile Pro<br>990             995             1000 | 3148 |
| cac ata gac cca tcg cgc cct atg acc ccc caa cag cga cgc ctg cag<br>His Ile Asp Pro Ser Arg Pro Met Thr Pro Gln Gln Arg Arg Leu Gln<br>1005             1010             1015 | 3196 |
| cag cga cgc cta caa cac cgc ctg cgg ctt cgg gca cag atg cgg ctg<br>Gln Arg Arg Leu Gln His Arg Leu Arg Leu Arg Ala Gln Met Arg Leu<br>1020             1025             1030             1035 | 3244 |

```
cgg cgc ctc aac gcc acc acc acc cta ggc ccc cac act gtg cct ccc         3292
Arg Arg Leu Asn Ala Thr Thr Thr Leu Gly Pro His Thr Val Pro Pro
                1040                1045                1050 acg ctg ccc cct gcc cct gcc acc acc ctg agc act acc ata gag ccc         3340
Thr Leu Pro Pro Ala Pro Ala Thr Thr Leu Ser Thr Thr Ile Glu Pro
                1055                1060                1065 tgg ggc ctc ata ccg cca acc acc gct ggc tgg gag gag tcg gag act         3388
Trp Gly Leu Ile Pro Pro Thr Thr Ala Gly Trp Glu Glu Ser Glu Thr
                1070                1075                1080 gag acc tac aca gag gtg gtg aca gag ttt ggg acc gag gtg gag ccc         3436
Glu Thr Tyr Thr Glu Val Val Thr Glu Phe Gly Thr Glu Val Glu Pro
                1085                1090                1095 gag ttt ggg acc aag gtg gag ccc gag ttt gag acc cag ttg gag cct         3484
Glu Phe Gly Thr Lys Val Glu Pro Glu Phe Glu Thr Gln Leu Glu Pro
1100                1105                1110                1115 gag ttc gag acc cag ctg gaa ccc gag ttt gag gaa gag gag gag gag         3532
Glu Phe Glu Thr Gln Leu Glu Pro Glu Phe Glu Glu Glu Glu Glu Glu
                1120                1125                1130 gag aaa gag gag gag ata gcc act ggc cag gca ttc ccc ttc aca aca         3580
Glu Lys Glu Glu Glu Ile Ala Thr Gly Gln Ala Phe Pro Phe Thr Thr
                1135                1140                1145 gta gag acc tac aca gtg aac ttt ggg gac ttc tgagatcagc gtcctaccaa       3633
Val Glu Thr Tyr Thr Val Asn Phe Gly Asp Phe
                1150                1155 gaccccagcc caactcaagc tacagcagca gcacttccca agcctgctga ccacagtcac       3693
atcacccatc agcacatgga aggcccctgg tatggacact gaaaggaagg gctggtcctg       3753 ccccttttgag ggggtgcaaa catgactggg acctaagagc cagaggctgt gtagaggctc      3813
ctgctccacc tgccagtctc gtaagagatg gggttgctgc agtgttggag tagggcaga       3873 gggagggagc caaggtcact ccaataaaac aagctcatgg caaaaaaaaa aaaaaaaaa        3933 aa                                                                       3935

<210> SEQ ID NO 2
<211> LENGTH: 1158
<212> TYPE: PRT
<213> ORGANISM: Homo sapiens

<400> SEQUENCE: 2

Met Ala Ala Val Arg Gly Ala Pro Leu Leu Ser Cys Leu Leu Ala Leu
 1               5                  10                  15

Leu Ala Leu Cys Pro Gly Gly Arg Pro Gln Thr Val Leu Thr Asp Asp
                20                  25                  30

Glu Ile Glu Glu Phe Leu Glu Gly Phe Leu Ser Glu Leu Glu Pro Glu
            35                  40                  45

Pro Arg Glu Asp Asp Val Glu Ala Pro Pro Pro Glu Pro Thr Pro
        50                  55                  60

Arg Val Arg Lys Ala Gln Ala Gly Gly Lys Pro Gly Lys Arg Pro Gly
65                  70                  75                  80

Thr Ala Ala Glu Val Pro Pro Glu Lys Thr Lys Asp Lys Gly Lys Lys
                85                  90                  95

Gly Lys Lys Asp Lys Gly Pro Lys Val Pro Lys Glu Ser Leu Glu Gly
            100                 105                 110

Ser Pro Arg Pro Pro Lys Lys Gly Lys Glu Lys Pro Lys Ala Thr
        115                 120                 125

Lys Lys Pro Lys Glu Lys Pro Pro Lys Ala Thr Lys Lys Pro Lys Glu
    130                 135                 140
```

```
Glu Pro Pro Lys Ala Thr Lys Lys Pro Lys Glu Lys Pro Lys Ala
145                 150                 155                 160

Thr Lys Lys Pro Pro Ser Gly Lys Arg Pro Pro Ile Leu Ala Pro Ser
                165                 170                 175

Glu Thr Leu Glu Trp Pro Leu Pro Pro Pro Ser Pro Gly Pro Glu
                180                 185                 190

Glu Leu Pro Gln Glu Gly Gly Ala Pro Leu Ser Asn Asn Trp Gln Asn
            195                 200                 205

Pro Gly Glu Glu Thr His Val Glu Ala Gln His Gln Pro Glu Pro
        210                 215                 220

Glu Glu Glu Thr Glu Gln Pro Thr Leu Asp Tyr Asn Asp Gln Ile Glu
225                 230                 235                 240

Arg Glu Asp Tyr Glu Asp Phe Glu Tyr Ile Arg Arg Gln Lys Gln Pro
                245                 250                 255

Arg Pro Pro Pro Ser Arg Arg Arg Pro Glu Arg Val Trp Pro Glu
                260                 265                 270

Pro Pro Glu Glu Lys Ala Pro Ala Pro Ala Pro Glu Glu Arg Ile Glu
            275                 280                 285

Pro Pro Val Lys Pro Leu Leu Pro Pro Leu Pro Pro Asp Tyr Gly Asp
        290                 295                 300

Gly Tyr Val Ile Pro Asn Tyr Asp Asp Met Asp Tyr Tyr Phe Gly Pro
305                 310                 315                 320

Pro Pro Pro Gln Lys Pro Asp Ala Glu Arg Gln Thr Asp Glu Glu Lys
                325                 330                 335

Glu Glu Leu Lys Lys Pro Lys Lys Glu Asp Ser Ser Pro Lys Glu Glu
            340                 345                 350

Thr Asp Lys Trp Ala Val Glu Lys Gly Lys Asp His Lys Glu Pro Arg
        355                 360                 365

Lys Gly Glu Glu Leu Glu Glu Glu Trp Thr Pro Thr Glu Lys Val Lys
    370                 375                 380

Cys Pro Pro Ile Gly Met Glu Ser His Arg Ile Glu Asp Asn Gln Ile
385                 390                 395                 400

Arg Ala Ser Ser Met Leu Arg His Gly Leu Gly Ala Gln Arg Gly Arg
                405                 410                 415

Leu Asn Met Gln Thr Gly Ala Thr Glu Asp Asp Tyr Tyr Asp Gly Ala
                420                 425                 430

Trp Cys Ala Glu Asp Asp Ala Arg Thr Gln Trp Ile Glu Val Asp Thr
        435                 440                 445

Arg Arg Thr Thr Arg Phe Thr Gly Val Ile Thr Gln Gly Arg Asp Ser
    450                 455                 460

Ser Ile His Asp Asp Phe Val Thr Thr Phe Phe Val Gly Phe Ser Asn
465                 470                 475                 480

Asp Ser Gln Thr Trp Val Met Tyr Thr Asn Gly Tyr Glu Glu Met Thr
                485                 490                 495

Phe His Gly Asn Val Asp Lys Asp Thr Pro Val Leu Ser Glu Leu Pro
            500                 505                 510

Glu Pro Val Val Ala Arg Phe Ile Arg Ile Tyr Pro Leu Thr Trp Asn
        515                 520                 525

Gly Ser Leu Cys Met Arg Leu Glu Val Leu Gly Cys Ser Val Ala Pro
    530                 535                 540

Val Tyr Ser Tyr Tyr Ala Gln Asn Glu Val Val Ala Thr Asp Asp Leu
545                 550                 555                 560
```

-continued

```
Asp Phe Arg His His Ser Tyr Lys Asp Met Arg Gln Leu Met Lys Val
            565                 570                 575
Val Asn Glu Glu Cys Pro Thr Ile Thr Arg Thr Tyr Ser Leu Gly Lys
        580                 585                 590
Ser Ser Arg Gly Leu Lys Ile Tyr Ala Met Glu Ile Ser Asp Asn Pro
    595                 600                 605
Gly Glu His Glu Leu Gly Glu Pro Glu Phe Arg Tyr Thr Ala Gly Ile
610                 615                 620
His Gly Asn Glu Val Leu Gly Arg Glu Leu Leu Leu Leu Met Gln
625                 630                 635                 640
Tyr Leu Cys Arg Glu Tyr Arg Asp Gly Asn Pro Arg Val Arg Ser Leu
            645                 650                 655
Val Gln Asp Thr Arg Ile His Leu Val Pro Ser Leu Asn Pro Asp Gly
        660                 665                 670
Tyr Glu Val Ala Ala Gln Met Gly Ser Glu Phe Gly Asn Trp Ala Leu
    675                 680                 685
Gly Leu Trp Thr Glu Glu Gly Phe Asp Ile Phe Glu Asp Phe Pro Asp
690                 695                 700
Leu Asn Ser Val Leu Trp Gly Ala Glu Glu Arg Lys Trp Val Pro Tyr
705                 710                 715                 720
Arg Val Pro Asn Asn Asn Leu Pro Ile Pro Glu Arg Tyr Leu Ser Pro
            725                 730                 735
Asp Ala Thr Val Ser Thr Glu Val Arg Ala Ile Ile Ala Trp Met Glu
        740                 745                 750
Lys Asn Pro Phe Val Leu Gly Ala Asn Leu Asn Gly Gly Glu Arg Leu
    755                 760                 765
Val Ser Tyr Pro Tyr Asp Met Ala Arg Thr Pro Thr Gln Glu Gln Leu
770                 775                 780
Leu Ala Ala Met Ala Ala Ala Arg Gly Glu Asp Glu Asp Glu Val
785                 790                 795                 800
Ser Glu Ala Gln Glu Thr Pro Asp His Ala Ile Phe Arg Trp Leu Ala
            805                 810                 815
Ile Ser Phe Ala Ser Ala His Leu Thr Leu Thr Glu Pro Tyr Arg Gly
        820                 825                 830
Gly Cys Gln Ala Gln Asp Tyr Thr Gly Gly Met Gly Ile Val Asn Gly
    835                 840                 845
Ala Lys Trp Asn Pro Arg Thr Gly Thr Ile Asn Asp Phe Ser Tyr Leu
850                 855                 860
His Thr Asn Cys Leu Glu Leu Ser Phe Tyr Leu Gly Cys Asp Lys Phe
865                 870                 875                 880
Pro His Glu Ser Glu Leu Pro Arg Glu Trp Glu Asn Asn Lys Glu Ala
            885                 890                 895
Leu Leu Thr Phe Met Glu Gln Val His Arg Gly Ile Lys Gly Val Val
        900                 905                 910
Thr Asp Glu Gln Gly Ile Pro Ile Ala Asn Ala Thr Ile Ser Val Ser
    915                 920                 925
Gly Ile Asn His Gly Val Lys Thr Ala Ser Gly Gly Asp Tyr Trp Arg
930                 935                 940
Ile Leu Asn Pro Gly Glu Tyr Arg Val Thr Ala His Ala Glu Gly Tyr
945                 950                 955                 960
Thr Pro Ser Ala Lys Thr Cys Asn Val Asp Tyr Asp Ile Gly Ala Thr
            965                 970                 975
Gln Cys Asn Phe Ile Leu Ala Arg Ser Asn Trp Lys Arg Ile Arg Glu
```

-continued

```
              980           985           990
Ile Met Ala Met Asn Gly Asn Arg Pro Ile Pro His Ile Asp Pro Ser
        995                1000               1005
Arg Pro Met Thr Pro Gln Gln Arg Arg Leu Gln Gln Arg Arg Leu Gln
        1010               1015               1020
His Arg Leu Arg Leu Arg Ala Gln Met Arg Leu Arg Arg Leu Asn Ala
1025               1030               1035               1040
Thr Thr Thr Leu Gly Pro His Thr Val Pro Pro Thr Leu Pro Pro Ala
                 1045               1050               1055
Pro Ala Thr Thr Leu Ser Thr Thr Ile Glu Pro Trp Gly Leu Ile Pro
        1060               1065               1070
Pro Thr Thr Ala Gly Trp Glu Glu Ser Glu Thr Glu Thr Tyr Thr Glu
        1075               1080               1085
Val Val Thr Glu Phe Gly Thr Glu Val Glu Pro Glu Phe Gly Thr Lys
1090               1095               1100
Val Glu Pro Glu Phe Glu Thr Gln Leu Glu Pro Glu Phe Glu Thr Gln
1105               1110               1115               1120
Leu Glu Pro Glu Phe Glu Glu Glu Glu Glu Lys Glu Glu Glu
                 1125               1130               1135
Ile Ala Thr Gly Gln Ala Phe Pro Phe Thr Thr Val Glu Thr Tyr Thr
                 1140               1145               1150
Val Asn Phe Gly Asp Phe
        1155

<210> SEQ ID NO 3
<211> LENGTH: 2743
<212> TYPE: DNA
<213> ORGANISM: Mus musculus

<400> SEQUENCE: 3
aagcttagtc tccctctctc ctggctcctc tcctggggct tccctatgga ggtagcactt    60
acagaagatg cttgttccaa accttcaggg gtacaaacta cacagatata ctgaaggaca   120
ggaggctggg gcctccccccc accccaaca gccactgttc tctcaggagc tctgcttctg   180
ctctgcagca ttgaaaacaa aactgaagga caccttcctt ctctcaggcc agcccagtgc   240
tgttgtgtga tccctcggga agactctaac gcattcacag ggacaacagg agttgggagg   300
gagaggagtt acagaacttt ccagcaggac ctcaggagaa cgcctggaca cggacaggaa   360
cccccaaccc ctcagggacc cccttggacc ctttgagtgc tcctgatcat ggaagccacc   420
agcctcccga ttcctcagct gtggccttgg cagtgccctc tggacatttg acttaaacgc   480
tatgctcttc agcagagtgg agagctctcc tcacaggctc tggcttctgg ttgtcctctt   540
gccccagcgc tgtgggccca ggttagaaag acttcctgag acaggctcc ctcaggagga   600
tccccagcgt acgactgtgc tcccacgcac ctttccggat tttctgtgtg gaggcctcaa   660
cccctcaggc ctcctgggcc agctcctctg ctcgaattcc tgtccgtgac tcattgaggc   720
tcaggaaaag gctttctaga ccttaggttt ctttgttttc catttttgaa atggcttctg   780
ttttccctgg cagagaatat ccaacccaaa ttcagtccaa gtatgaccca tgcctaggga   840
agtgacatcc atgtccctc atgcaccctg tggcataccc agcatgacac actgaccag    900
actgggggca cggaagccaa ttcccagaac tgactttgag cacaatgatt cagagggtga   960
ccatgagtga gacttgcttt actcttgctc tgcgaccagg ttgaagtctc tcatgggag   1020
gcctagctgt gagaggattg tcctgggatg ggggaagggg gagcaaagtg gatgaggacc   1080
```

-continued

```
aacagcctgt gggatgcaag ggctgatcgt gtgtgctagg cacagcacaa agtggtccat    1140
ttagccgggc agtggtggtg cacacccttta atcccagcac ttgggaggca gcagcaggtg   1200
ggtttctgag ttcgaggcca gcctggtcta cagagcaagt tccaggacag ccagagctac    1260
acagagaaac tctgtctcaa aaaaatcgaa taaaccagaa aggtggtcca tttaatatgc    1320
gtatagtaag ttgtggacac gggagttccc ctgctgagtc agacagctag gagggctaag    1380
atgggttaga ccctccccccc ccccacacac acacacacac actcacacac acatcagttc    1440
ttggcatagt ctccatgctt cctcaaggag agccagaaag gagactgccg ggaggagctt    1500
gcctactccc tgagagcagt gggttacaga gcccagtgcc cgaaaatttc cccttttttct   1560 ccctgctcat gctggacaga gagggtgagg gtgagggtga agactgagg aggtggcatc     1620 gtgttggtgt tcttgacct gctttttctt ttttctcttc cagctgagat gtaaactttc     1680
ccatgtcaat catctggggg tcgctattct tttttatcag agtgcctccc caccttggtt    1740
gaaagctgcc tgccactacc ctggacctat ggctgctaca agcccacgtt cacatcttta    1800
atccttcatg ggtaaatgct ctggcattcc tgggcttagc tatgatggcc attatgagcc    1860
agccaacgtt tgtattctag aagccatagc tgaagctgtt gtaaacaatt tgttgtttta    1920
accgcttctg gtcagaggaa ggagagaata gctattactc cacattggga cctgagccct    1980
gagctctgaa gtgggctcc tatctccata aggacagcag cttgctgaga acagcttttc     2040
acagccttcc tcgcaaaaat tggctccaaa gacctgggat gttggtgata actggacaaa    2100
ggtgacacct gtgcaagcac acagcaggtg acactttgaa gagctaacct ccagaaagtg    2160
gaaaggaggt gatcgccagt accctcgagg gccctactcc ctccctcccc tagcaatctc    2220
cctgggctca gagcaaaggg cacagcgggt tagagcacag gtctccttag actccgcaca    2280
ctcccttccc cataactgtt gcattctttt ctcccaggcc ttcctccccg ctaggcgccc    2340
tgcacccaga ccctctaaac tggcgcgtga cgctgctatt agtctgggct ccgtgctgtc    2400
cgcctccctc ccccgcagcc cccggtccaa ggccggctcc tcctcctccc cctccggaaa    2460
cccgaagccc ccgccccggc caggccgtcg caagcgctct ggagggcggt ccgcgtgaga    2520
gccagccacg cggggcagga gcgcccagtt gctgccggag ctgggcccgc cagaacctct    2580
cctggagccc cttgctctcc ttgaatctcc ctttcccacc gctttctgga tacccttgac    2640
gcccacgttc ctcgcgccct ttcccgcccc tacgcggggc gctgcccctg ccacccaagt    2700
ccctgctcaa gcccgcccgg tcccgcgcgt gcccagagcc atg                     2743
```

<210> SEQ ID NO 4
<211> LENGTH: 17
<212> TYPE: DNA
<213> ORGANISM: Mus musculus

<400> SEQUENCE: 4

```
atctggttgt cctcaat                                                   17
```

<210> SEQ ID NO 5
<211> LENGTH: 17
<212> TYPE: DNA
<213> ORGANISM: Mus musculus

<400> SEQUENCE: 5

```
tgactccatc ccaatag                                                   17
```

<210> SEQ ID NO 6
<211> LENGTH: 26

```
<212> TYPE: DNA
<213> ORGANISM: Mus musculus

<400> SEQUENCE: 6
cggaattcag tccctgctca agcccg                                              26

<210> SEQ ID NO 7
<211> LENGTH: 28
<212> TYPE: DNA
<213> ORGANISM: Mus musculus

<400> SEQUENCE: 7
cgaagcttga agtccccaaa gttcactg                                            28

<210> SEQ ID NO 8
<211> LENGTH: 1128
<212> TYPE: PRT
<213> ORGANISM: Mus musculus

<400> SEQUENCE: 8
```

| | | | | | | | | | | | | | | |
|---|---|---|---|---|---|---|---|---|---|---|---|---|---|---|
| Met | Ala | Pro | Val | Arg | Thr | Ala | Ser | Leu | Leu | Cys | Gly | Leu | Leu | Ala | Leu |
| 1 | | | | 5 | | | | | 10 | | | | | 15 | |
| Leu | Thr | Leu | Cys | Pro | Glu | Gly | Asn | Pro | Gln | Thr | Val | Leu | Thr | Asp | Asp |
| | | | 20 | | | | | 25 | | | | | 30 | | |
| Glu | Ile | Glu | Glu | Phe | Leu | Glu | Gly | Phe | Leu | Ser | Glu | Leu | Glu | Thr | Gln |
| | | 35 | | | | | 40 | | | | | 45 | | | |
| Ser | Pro | Pro | Arg | Glu | Asp | Asp | Val | Glu | Val | Gln | Pro | Leu | Pro | Glu | Pro |
| | 50 | | | | | 55 | | | | | 60 | | | | |
| Thr | Gln | Arg | Pro | Arg | Lys | Ser | Lys | Ala | Gly | Gly | Lys | Gln | Arg | Ala | Asp |
| 65 | | | | | 70 | | | | | 75 | | | | | 80 |
| Val | Glu | Val | Pro | Pro | Glu | Lys | Asn | Lys | Asp | Lys | Glu | Lys | Lys | Gly | Lys |
| | | | | 85 | | | | | 90 | | | | | 95 | |
| Lys | Asp | Lys | Gly | Pro | Lys | Ala | Thr | Lys | Pro | Leu | Glu | Gly | Ser | Thr | Arg |
| | | | 100 | | | | | 105 | | | | | 110 | | |
| Pro | Thr | Lys | Lys | Pro | Lys | Glu | Lys | Pro | Pro | Lys | Ala | Thr | Lys | Lys | Pro |
| | | 115 | | | | | 120 | | | | | 125 | | | |
| Lys | Glu | Lys | Pro | Pro | Lys | Ala | Thr | Lys | Lys | Pro | Lys | Glu | Lys | Pro | Pro |
| | 130 | | | | | 135 | | | | | 140 | | | | |
| Lys | Ala | Thr | Lys | Lys | Pro | Lys | Glu | Lys | Pro | Pro | Lys | Ala | Thr | Lys | Arg |
| 145 | | | | | 150 | | | | | 155 | | | | | 160 |
| Pro | Ser | Ala | Gly | Lys | Lys | Phe | Ser | Thr | Val | Ala | Pro | Leu | Glu | Thr | Leu |
| | | | | 165 | | | | | 170 | | | | | 175 | |
| Asp | Arg | Leu | Leu | Pro | Ser | Pro | Ser | Asn | Pro | Ser | Ala | Gln | Glu | Leu | Pro |
| | | | 180 | | | | | 185 | | | | | 190 | | |
| Gln | Lys | Arg | Asp | Thr | Pro | Phe | Pro | Asn | Ala | Trp | Gln | Gly | Gln | Gly | Glu |
| | | 195 | | | | | 200 | | | | | 205 | | | |
| Glu | Thr | Gln | Val | Glu | Ala | Lys | Gln | Pro | Arg | Pro | Glu | Pro | Glu | Glu | Glu |
| | 210 | | | | | 215 | | | | | 220 | | | | |
| Thr | Glu | Met | Pro | Thr | Leu | Asp | Tyr | Asn | Asp | Gln | Ile | Glu | Lys | Glu | Asp |
| 225 | | | | | 230 | | | | | 235 | | | | | 240 |
| Tyr | Glu | Asp | Phe | Glu | Tyr | Ile | Arg | Arg | Gln | Lys | Gln | Pro | Arg | Pro | Thr |
| | | | | 245 | | | | | 250 | | | | | 255 | |
| Pro | Ser | Arg | Arg | Arg | Leu | Trp | Pro | Glu | Arg | Pro | Glu | Glu | Lys | Thr | Glu |
| | | | 260 | | | | | 265 | | | | | 270 | | |
| Glu | Pro | Glu | Glu | Arg | Lys | Glu | Val | Glu | Pro | Pro | Leu | Lys | Pro | Leu | Leu |
| | | 275 | | | | | 280 | | | | | 285 | | | |

```
Pro Pro Asp Tyr Gly Asp Ser Tyr Val Ile Pro Asn Tyr Asp Asp Leu
    290                 295                 300

Asp Tyr Tyr Phe Pro His Pro Pro Gln Lys Pro Asp Val Gly Gln
305                 310                 315                 320

Glu Val Asp Glu Glu Lys Glu Met Lys Lys Pro Lys Lys Glu Gly
                325                 330                 335

Ser Ser Pro Lys Glu Asp Thr Glu Asp Lys Trp Thr Val Glu Lys Asn
            340                 345                 350

Lys Asp His Lys Gly Pro Arg Lys Gly Glu Glu Leu Glu Glu Glu Trp
        355                 360                 365

Ala Pro Val Glu Lys Ile Lys Cys Pro Pro Ile Gly Met Glu Ser His
370                 375                 380

Arg Ile Glu Asp Asn Gln Ile Arg Ala Ser Ser Met Leu Arg His Gly
385                 390                 395                 400

Leu Gly Ala Gln Arg Gly Arg Leu Asn Met Gln Ala Gly Ala Asn Glu
                405                 410                 415

Asp Asp Tyr Tyr Asp Gly Ala Trp Cys Ala Glu Asp Glu Ser Gln Thr
            420                 425                 430

Gln Trp Ile Glu Val Asp Thr Arg Arg Thr Thr Arg Phe Thr Gly Val
        435                 440                 445

Ile Thr Gln Gly Arg Asp Ser Ser Ile His Asp Phe Val Thr Thr
450                 455                 460

Phe Phe Val Gly Phe Ser Asn Asp Ser Gln Thr Trp Val Met Tyr Thr
465                 470                 475                 480

Asn Gly Tyr Glu Glu Met Thr Phe Tyr Gly Asn Val Asp Lys Asp Thr
                485                 490                 495

Pro Val Leu Ser Glu Leu Pro Glu Pro Val Val Ala Arg Phe Ile Arg
            500                 505                 510

Ile Tyr Pro Leu Thr Trp Asn Gly Ser Leu Cys Met Arg Leu Glu Val
        515                 520                 525

Leu Gly Cys Pro Val Thr Pro Val Tyr Ser Tyr Tyr Ala Gln Asn Glu
530                 535                 540

Val Val Thr Thr Asp Ser Leu Asp Phe Arg His His Ser Tyr Lys Asp
545                 550                 555                 560

Met Arg Gln Leu Met Lys Ala Val Asn Glu Glu Cys Pro Thr Ile Thr
                565                 570                 575

Arg Thr Tyr Ser Leu Gly Lys Ser Ser Arg Gly Leu Lys Ile Tyr Ala
            580                 585                 590

Met Glu Ile Ser Asp Asn Pro Gly Asp His Glu Leu Gly Glu Pro Glu
        595                 600                 605

Phe Arg Tyr Thr Ala Gly Ile His Gly Asn Glu Val Leu Gly Arg Glu
610                 615                 620

Leu Leu Leu Leu Leu Met Gln Tyr Leu Cys Gln Glu Tyr Arg Asp Gly
625                 630                 635                 640

Asn Pro Arg Val Arg Asn Leu Val Gln Asp Thr Arg Ile His Leu Val
                645                 650                 655

Pro Ser Leu Asn Pro Asp Gly Tyr Glu Val Ala Ala Gln Met Gly Ser
            660                 665                 670

Glu Phe Gly Asn Trp Ala Leu Gly Leu Trp Thr Glu Gly Phe Asp
        675                 680                 685

Ile Phe Glu Asp Phe Pro Asp Leu Asn Ser Val Leu Trp Ala Ala Glu
        690                 695                 700

Glu Lys Lys Trp Val Pro Tyr Arg Val Pro Asn Asn Asn Leu Pro Ile
```

-continued

```
                705                 710                 715                 720

Pro Glu Arg Tyr Leu Ser Pro Asp Ala Thr Val Ser Thr Glu Val Arg
                725                 730                 735

Ala Ile Ile Ser Trp Met Glu Lys Asn Pro Phe Val Leu Gly Ala Asn
                740                 745                 750

Leu Asn Gly Gly Glu Arg Leu Val Ser Tyr Pro Tyr Asp Met Ala Arg
                755                 760                 765

Thr Pro Ser Gln Glu Gln Leu Leu Ala Glu Ala Leu Ala Ala Ala Arg
                770                 775                 780

Gly Glu Asp Asp Gly Val Ser Glu Ala Gln Glu Thr Pro Asp His
785                 790                 795                 800

Ala Ile Phe Arg Trp Leu Ala Ile Ser Phe Ala Ser Ala His Leu Thr
                805                 810                 815

Met Thr Glu Pro Tyr Arg Gly Gly Cys Gln Ala Gln Asp Tyr Thr Ser
                820                 825                 830

Gly Met Gly Ile Val Asn Gly Ala Lys Trp Asn Pro Arg Ser Gly Thr
                835                 840                 845

Phe Asn Arg Phe Ser Tyr Leu His Thr Asn Cys Leu Glu Leu Ser Val
                850                 855                 860

Tyr Leu Gly Cys Asp Lys Phe Pro His Glu Ser Glu Leu Pro Arg Glu
865                 870                 875                 880

Trp Glu Asn Asn Lys Glu Ala Leu Leu Thr Phe Met Glu Gln Val His
                885                 890                 895

Arg Gly Ile Lys Gly Val Val Thr Asp Glu Gln Gly Ile Pro Ile Ala
                900                 905                 910

Asn Ala Thr Ile Ser Val Ser Gly Ile Asn His Gly Val Lys Thr Ala
                915                 920                 925

Ser Gly Gly Asp Tyr Trp Arg Ile Leu Asn Pro Gly Glu Tyr Arg Val
                930                 935                 940

Thr Ala His Ala Glu Gly Tyr Thr Ser Ser Ala Lys Ile Cys Asn Val
945                 950                 955                 960

Asp Tyr Asp Ile Gly Ala Thr Gln Cys Asn Phe Ile Leu Ala Arg Ser
                965                 970                 975

Asn Trp Lys Arg Ile Arg Glu Ile Leu Ala Met Asn Gly Asn Arg Pro
                980                 985                 990

Ile Leu Gly Val Asp Pro Ser Arg Pro Met Thr Pro Gln Gln Arg Arg
                995                 1000                1005

Met Gln Gln Arg Arg Leu Gln Tyr Arg Leu Arg Met Arg Glu Gln Met
            1010                1015                1020

Arg Leu Arg Arg Leu Asn Ser Thr Ala Gly Pro Ala Thr Ser Pro Thr
1025                1030                1035                1040

Pro Ala Leu Met Pro Pro Ser Pro Thr Pro Ala Ile Thr Leu Arg
                1045                1050                1055

Pro Trp Glu Val Leu Pro Thr Thr Ala Gly Trp Glu Glu Ser Glu
                1060                1065                1070

Thr Glu Thr Tyr Thr Glu Val Val Thr Glu Phe Glu Thr Glu Tyr Gly
                1075                1080                1085
```

-continued

```
Thr Asp Leu Glu Val Glu Glu Ile Glu Glu Glu Glu Glu Glu
    1090            1095             1100

Glu Glu Met Asp Thr Gly Leu Thr Phe Pro Leu Thr Thr Val Glu Thr
1105             1110             1115             1120

Tyr Thr Val Asn Phe Gly Asp Phe
                1125
```